United States Patent [19]

Sreekrishna et al.

[11] Patent Number: 5,707,828
[45] Date of Patent: *Jan. 13, 1998

[54] **EXPRESSION OF HUMAN SERUM ALBUMIN IN *PICHIA PASTORIS***

[75] Inventors: Kotikanyadan Sreekrishna, Bartlesville, Okla.; Juerg F. Tschopp, San Diego, Calif.; Gregory P. Thill, San Diego, Calif.; Russell A. Brierley, San Diego, Calif.; Kathryn A. Barr, Bartlesville, Okla.

[73] Assignee: Research Corporation Technologies, Inc., Tucson, Ariz.

[*] Notice: The term of this patent shall not extend beyond the expiration date of Pat. No. 5,330,901.

[21] Appl. No.: 433,037

[22] Filed: May 3, 1995

Related U.S. Application Data

[63] Continuation of Ser. No. 691,604, Apr. 25, 1991, abandoned.

[51] Int. Cl.$^6$ .............................. C12P 21/06; C12N 1/19; C12N 15/00; C12N 15/63
[52] U.S. Cl. ...................... 435/69.1; 435/69.6; 435/69.8; 435/172.1; 435/255.5; 435/320.1; 935/22; 935/28; 935/33; 935/37; 935/66; 935/69
[58] Field of Search .............................. 435/68.1, 69.6, 435/69.8, 172.1, 255.5, 320.1; 935/22, 28, 33, 37, 66, 69

[56] References Cited

U.S. PATENT DOCUMENTS

| | | | |
|---|---|---|---|
| 4,775,622 | 10/1988 | Hitzeman | 435/69.4 |
| 4,808,537 | 2/1989 | Stroman et al. | 435/6 |
| 4,837,148 | 6/1989 | Cregg | 435/172.3 |
| 4,855,231 | 8/1989 | Stroman et al. | 435/69.1 |
| 4,882,279 | 11/1989 | Cregg | 435/172.3 |
| 4,885,242 | 12/1989 | Cregg | 435/69.1 |
| 4,895,800 | 1/1990 | Tschopp et al. | 435/69.3 |

FOREIGN PATENT DOCUMENTS

| | | |
|---|---|---|
| 0 073 646 | 8/1982 | European Pat. Off. |
| 0 206 733 | 6/1986 | European Pat. Off. |
| 0 248 637 | 6/1987 | European Pat. Off. |
| 0 251 744 | 6/1987 | European Pat. Off. |
| 0 256 421 | 8/1987 | European Pat. Off. |
| 0 344 459 | 12/1989 | European Pat. Off. |

OTHER PUBLICATIONS

Bitter et al., "Expresion of Heterologous Genes in *Saccharomyces cerevisiae* from Vectors Utilizing the Glyceraldehyde-3-Phosphate Dehydrogenase Gene Promoter," *Gene*, 32: 268-274 (Dec. 1984).

Digan et al., "Secretion of Heterologous Proteins from the Methylotrophic Yeast *Pichia pastoris*," *Developments in Industrial Microbiology*, 29(supp 3): 59-65 (1988).

A. Dugaiczyk, "Nucleotide Sequence and the Encoded Amino Acids of Human Serum Albumin mRNA," *Proc. Natl. Acad. Sci. U.S.A.*, 79, 71-75 (Jan. 1982).

Ellis et al., "Isolation of Alcohol Oxidase and Two Other Methanol Regulatable Genes from the Yeast *Pichia pastoria*," *Mol. Cell. Biol.*, 5(5): 1111-1121.

T. Etcheverry, "Regulation of the Chelatin Promoter During the Expression of Human Serum Albumin or Yeast Phoshpoglycerate Kinase in Yeast," *Bio/Technology*, 4: 726-730 (Aug. 1986).

M. Latta, "Synthesis and Purification of Mature Human Serum Albumin from *E. coli*," *Nuc. Acid. Res.*, 9(22): 6103-6114 (Nov. 1981).

T. Nobuhira et al., "Amino Acid Substitution on Genetic Variants of Human Serum Albumin," *Proc. Natl. Acad. Sci. U.S.A.*, 84: 4413-4417 (Jul. 1987).

J. Peters, *Albumins: Structure, Biosynthesis, Function*, pp. 11-17 (1977).

C. Saunders, "Secretion of Human Serum Albumin from *Bacillus subtilis*," *J. Bacteriology*, 169(7): 2917-2925 (Jul. 1987).

Sleep et al., "The Secretion of Human Serum Albumin from the Yeast *Saccharomyces cerevisiae* Using Five Different Leader Sequences," *Bio/Technology*, 8: 42-46 (Jan. 1990).

Chemical Abstracts, vol. 107, No. 1, Jul. 6, 1987, p. 533, Abstract No. 5669u.

Abstract of JP 60248181, published Dec. 7, 1985.
Abstract of EP 123544, published Jul. 16, 1986.
Abstract of EP 91527, published Oct. 19, 1983.
Abstract of EP 20123, published Dec. 10, 1980.

*Primary Examiner*—Douglas W. Robinson
*Assistant Examiner*—Thanda Wai
*Attorney, Agent, or Firm*—Scully, Scott, Murphy & Presser

[57] ABSTRACT

The present invention is directed to expression cassettes comprising a 5' regulatory region from at least one of the *Pichia pastoris* AOXI gene, p40 gene, DASI gene or HIS4 gene, operably linked to an HSA structural gene including the HSA signal sequence. The HSA structural gene has a translational start codon within 0 to 11 deoxyribonucleotides from the 5' end of the HSA structural gene and is operably linked to a 3' termination sequence. Further, the adenine and thymine content of the intervening deoxyribonucleotides is in the range from about 55 to about 64%. The expression cassette may be an autonomously replicating vector or an integrative vector. Other embodiments of the present invention include *Pichia pastoris* strains transformed with the HSA expression cassettes and processes for secretion of HSA using the expression cassettes.

34 Claims, 6 Drawing Sheets

EXPRESSION OF HUMAN SERUM ALBUMIN IN *PICHIA PASTORIS*

This is a continuation of application Ser. No. 07/691,604, filed on Apr. 25, 1991, now abandoned.

FIELD OF THE INVENTION

This invention relates to the field of recombinant DNA biotechnology. In one aspect, this invention relates to a process for the expression of human serium albumin (HSA) in *Pichia pastoris*.

BACKGROUND

Human serum albumin is the most abundant plasma protein of adults. The concentration of albumin is 40 mg/ml, or 160 g of albumin circulating throughout the human body for a 70 kg adult male. This protein maintains osmotic pressure and functions in the binding and transport of copper, nickel, calcium (weakly, at 2–3 binding sites), bilirubin and protoporphyrin, long-chain fatty acids, prostaglandins, steroid hormones (weak binding with these hormones promotes their transfer across the membranes), thyroxine, triiodothyronine, and glutathione. According to Peters, T. and Reed, R. G. in *Albumin: Structure, Biosynthesis and Function*, (Peters, T. and Sjoholm, J. eds.) 1977 p.11–20, over 10,000 kilograms of purified albumin are administered annually in the United States alone to patients with circulatory failure or with albumin depletion.

Currently the only commercial source of HSA is from fractionated blood. Considering the possible dangers of blood borne contaminants and pathogens, it would be a considerable contribution to the commercial production of HSA to develop alternate methods of producing HSA. With the advent of recombinant DNA technology, it is now possible to produce HSA by alternate methods.

HSA has also been expressed in *Saccharomyces cerevisiae* as disclosed by Etcheverry et al. in *Bio/technology*, August 1986, p. 726 and Arjum Singh in EPA 123,544. Etcheverry disclosed HSA expression intracellularly in a concentration of approximately 6 mg/l and the presence of cell-associated HSA. Hayasuke et al. also disclosed the expression of HSA in *Saccharomyces cerevisiae* in combination with the GAL 1 promoter and a signal sequence. Hayasuke et al. appears to have been able to achieve a secreted production level of 160 mg/L. As described in EPA344,459, HSA has also been expressed in *Pichia pastoris* as intracellular or cell-associated protein. Although the expression of HSA in yeast cells, such as *Saccharomyces cerevisiae* and *Pichia pastoris*, is a significant step toward providing safe alternative sources of HSA, the expression of HSA as an intracellular or cell-associated protein is not desirable. Expensive and time consuming measures are required to recover and purify intracellular or cell-associated HSA. Furthermore, it would also be advantageous if a high level of HSA secretion could be achieved to improve the yields and lower the production costs.

Thus, it would be a significant contribution to the art to provide yeast strains which secrete high levels of HSA.

It also would be a significant contribution to the art to develop a process which produces HSA in a manner that is easy to recover and purify.

Therefore, it is an object of this invention to provide strains which produce high levels of HSA.

It is a further object of this invention to provide a process which produces HSA in a manner that is easy to recover and purify.

Other objects and advantages of the present invention will be apparent to those skilled in the art from the present specification.

SUMMARY OF THE INVENTION

In accordance with the present invention there has been discovered an improved expression cassette for the production of HSA in *Pichia pastoris* comprising
 a) a 5' *Pichia pastoris* regulatory region having a 5' end and a 3' end selected from the group consisting of the *Pichia pastoris* AOX1 regulatory region and the *Pichia pastoris* DAS1 regulatory region wherein the 3' end of the regulatory region is operably linked to
 b) an HSA structural gene encoding a signal sequence and mature protein having a 5' end and a 3' end wherein the HSA structural gene has an ATG start codon within about 6 deoxyribonucleotides of the 5' end of said HSA structural gene; and operably linked to
 c) a 3' termination sequence.

In accordance with the present invention there has also been discovered *Pichia pastoris* strains transformed with an improved expression cassette for the production of HSA in *Pichia pastoris* comprising
 a) a 5' *Pichia pastoris* regulatory region having a 5' end and a 3' end selected from the group consisting of the *Pichia pastoris* AOX1 regulatory region and the *Pichia pastoris* DAS1 regulatory region wherein the 3' end of the regulatory region is operably linked to
 b) an HSA structural gene encoding a signal sequence and mature protein having a 5' end and a 3' end wherein the HSA structural gene has an ATG start codon within about 6 deoxyribonucleotides of the 5' end of said HSA structural gene; and operably linked to
 c) a 3' termination sequence.

In a further embodiment of the present invention, there has also been discovered a process for the secretion of HSA from transformed *Pichia pastoris* cells comprising
 a) transforming *Pichia pastoris* with at least one vector having at least one expression cassette comprising
  i) a 5' *Pichia pastoris* regulatory region having a 5' end and a 3' end selected from the group consisting of the *Pichia pastoris* AOX1 regulatory region and the *Pichia pastoris* DAS1 regulatory region wherein the 3' end of the regulatory region is operably linked to
  ii) an HSA structural gene encoding a signal sequence and mature protein having a 5' end and a 3' end wherein the HSA structural gene has an ATG start codon within about 6 deoxyribonucleotides of the 5' end of said HSA structural gene; and operably linked to
  iii) a 3' termination sequence; and then
 b) culturing the resulting transformed *Pichia pastoris* under suitable conditions to obtain the secretion of HSA.

DETAILED DESCRIPTION OF THE FIGURES

Figure 1:
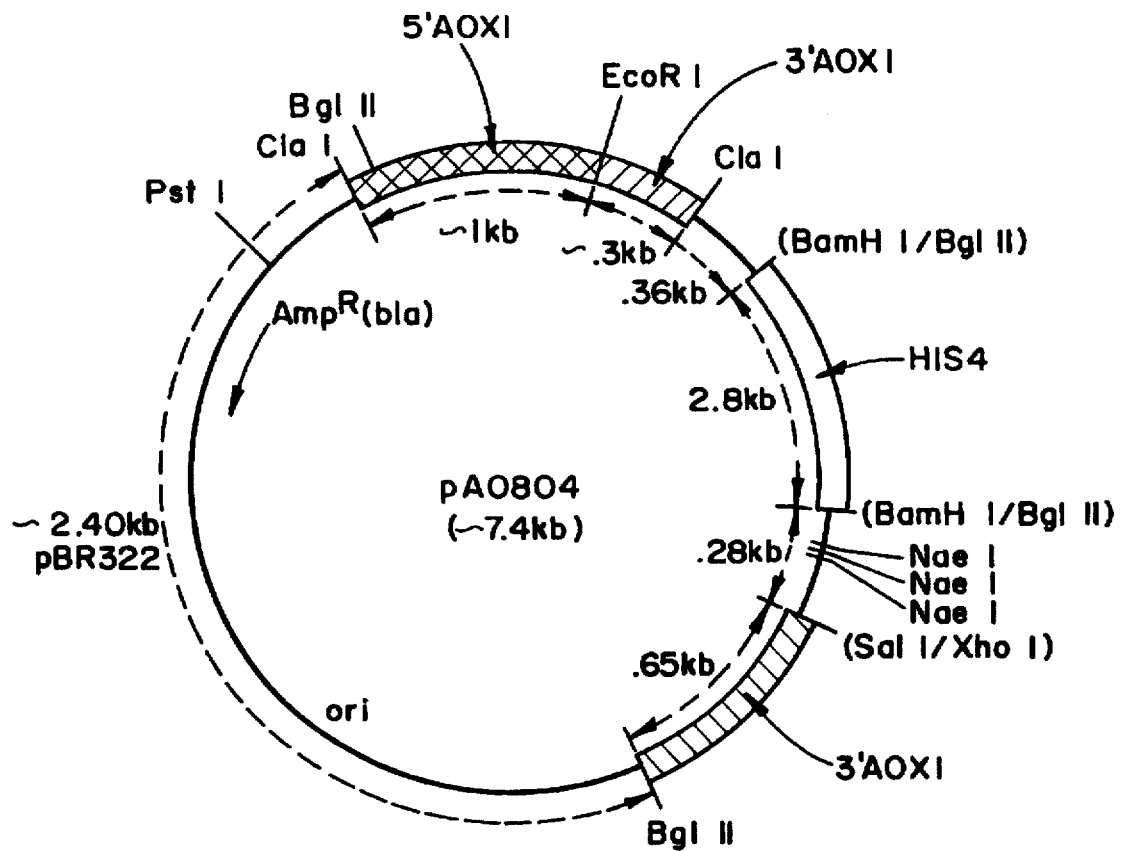

FIG. 1 provides a representation of plasmid pAO804 which contains a linear site-specific integrative vector in the fragment clockwise from BglII to BglII. The structural gene may be inserted in the unique EcoRI site of this plasmid. This plasmid may be recovered from the plasmid DNA of NRRL B-18114 by EcoRI digest and gel electrophoresis to recover a linear ~7.4 kb EcoRI fragment corresponding to FIG. 1.

Figure 2:
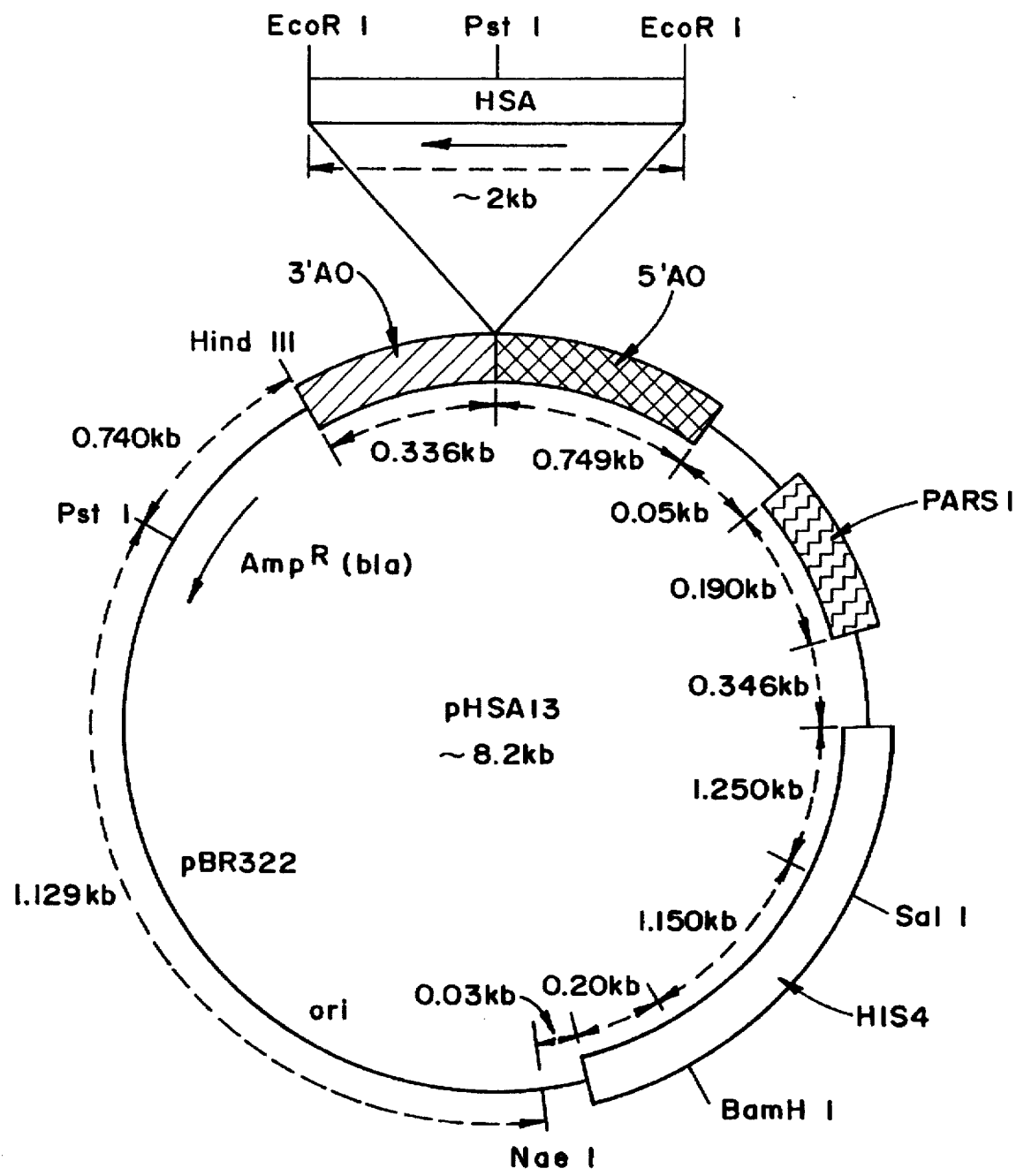

FIG. 2 provides a representation of pHSA13 in circular form.

Figure 3:
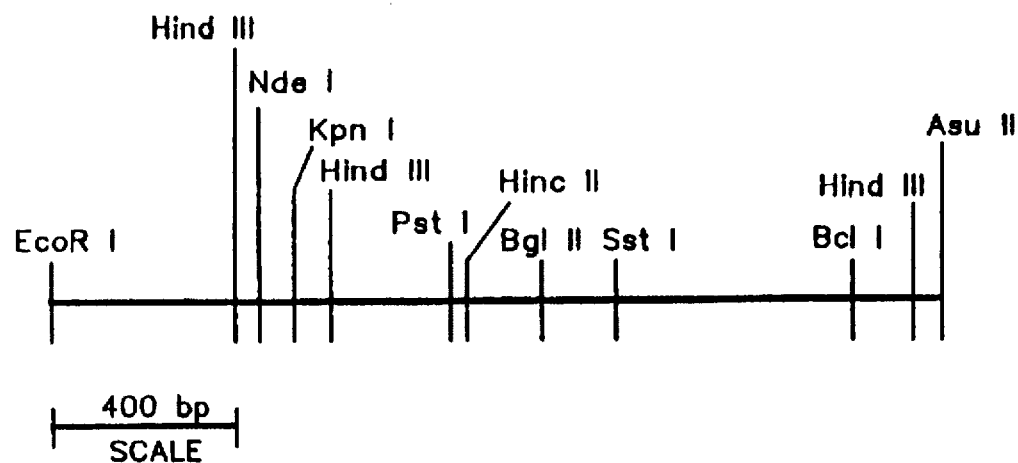

FIG. 3 provides a restriction map of the AOX1 5' regulatory region isolated from *Pichia pastoris*.

Figure 4:
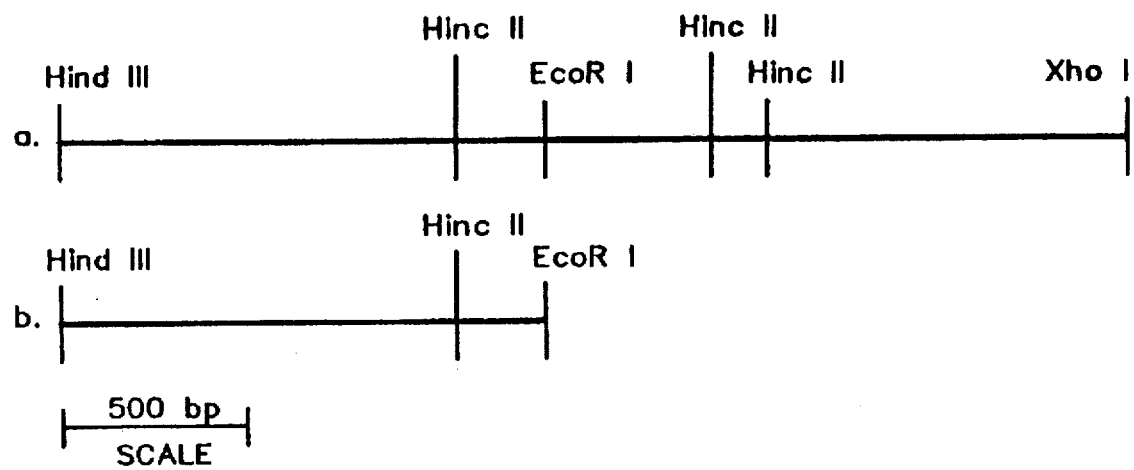

FIG. 4 provides a restriction map of the DAS1 5' regulatory region isolated from *Pichia pastoris*.

Figure 5:
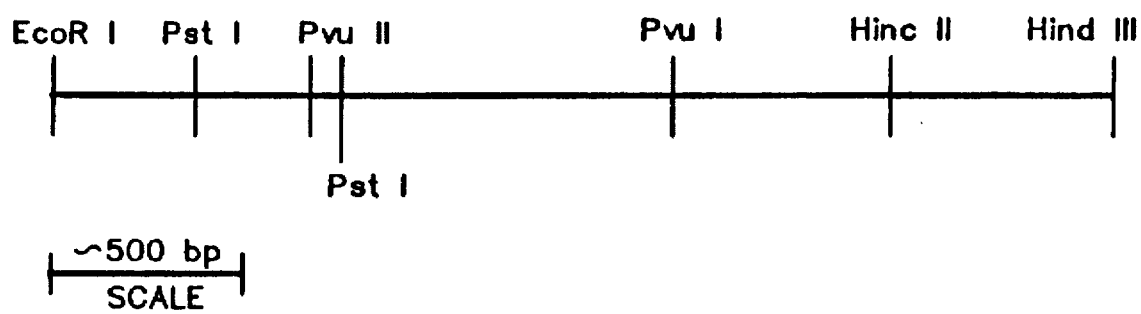

FIG. 5 provides a restriction map of the AOX1 3' termination sequence isolated from *Pichia pastoris*.

Figure 6:
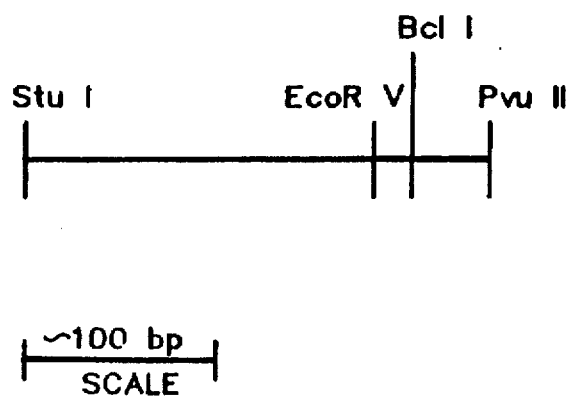

FIG. 6 provides a restriction map of the DAS1 3' termination sequence isolated from *Pichia pastoris*.

Figure 7:
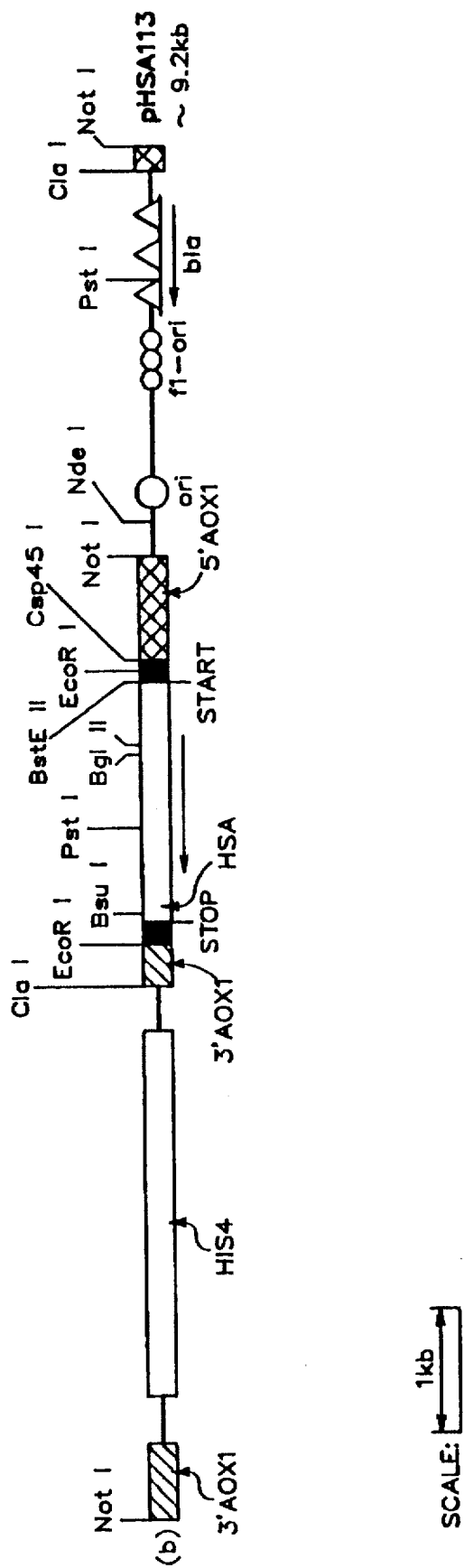

FIG. 7 provides a representation of pHSA113 in linear form.

Figure 8:
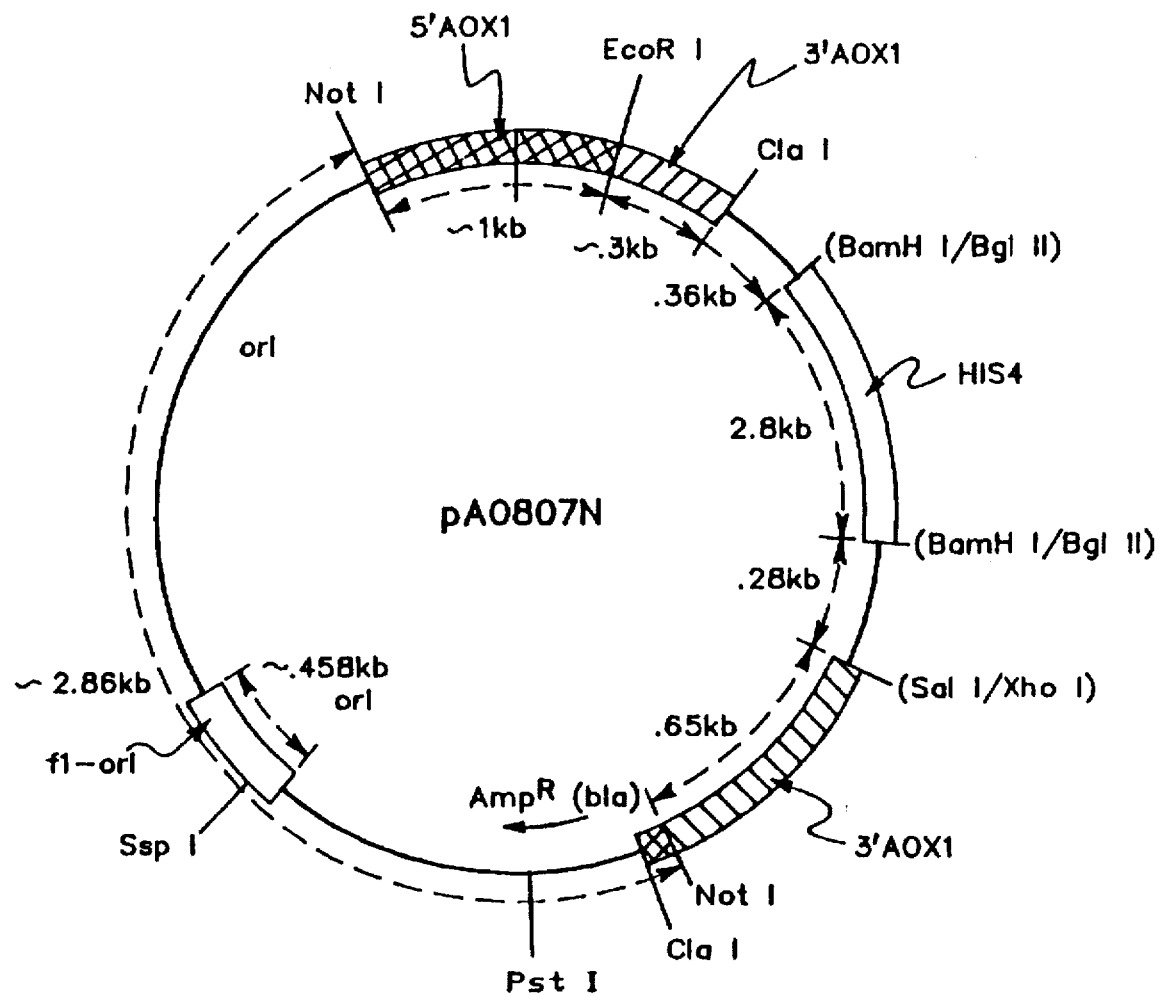

FIG. 8 provides a representation of plasmid pAO807N which contains a linear site-specific integrative vector in the fragment clockwise from NotI to NotI. The structural gene may be inserted in the unique EcoRI site of this plasmid.

DETAILED DESCRIPTION

The present invention provides improved expression cassettes for the expression of HSA, improved vectors and *Pichia pastoris* strains transformed with these improved cassettes and vectors.

Utilizing the present invention, HSA secretion levels of approximately 1–3.4 grams of authentic HSA per liter of fermentation broth have been obtained with an additional 15–88 µg HSA per mg of protein being present within the cell secretory pathway. This invention thus provides a means for the high level secretion of HSA. Achieving these levels of HSA production is a significant advancement over the prior production levels, since at the level of 1–3.4 grams per liter the recovery of HSA in high yields with high purities is possible.

To express the HSA structural gene, the gene must be operably linked to a 5' regulatory region and a 3' termination sequence, which forms an expression cassette which will be inserted into a host (usually a microorganism) via a vector (such as a circular plasmid or linear site-specific integrative vector). Operably linked as used in this context refers to a juxtaposition wherein the 5' regulatory region, structural gene, and 3' termination sequence are linked and configured so as to perform their normal function. 5' regulatory region or promoter as used herein means DNA sequences which respond to various stimuli and provide enhanced rates of mRNA transcription. 3' termination sequences are sequences 3' to the stop codon of a structural gene which function to stabilize the mRNA transcription product of the gene to which the sequence is operably linked (such as sequences which elicit polyadenylation). For the practice of this invention, it is preferred that the ATG of the structural gene be linked with as few intervening deoxyribonucleotides as possible to the 3' end of the 5' regulatory region, preferably about 11 or less deoxyribonucleotides and most preferably 8 or less deoxyribonucleotides. It is also preferred that the adenine and thymine content of the intervening deoxyribonucleotides be in the range of from about 55 percent to about 64 percent. Further, it appears that there are nucleotide preferences for certain specific locations. Counting in a 3' to 5' direction from the ATG codon of the structural gene with the first position in a 3' to 5' direction being the −1 position it appears that adenine or cytosine is the most preferred deoxyribonucleotide, in the −2 position the most preferred deoxyribonucleotide is either adenine or thymine, in the −3 position the most preferred deoxyribonucleotide is adenine or thymine and the most preferred nucleotide at the −4 position is adenine, thymine or cytosine. Currently, it is preferred that the AOX1 or DAS1 5' regulatory regions having the restriction maps of FIGS. 3 and 4 or, the sequences provided as SEQ ID No: 1 and SEQ ID No: 2, respectively, be linked at their 3' end of the sequence to the ATG start codon of the HSA structural gene. Two examples of appropriate linkages for the AOX1 5' regulatory region are illustrated below.

| Construct Designation | End of the 5' Regulatory Region for AOX1 | Deoxyribonucleotide intervening before ATG start codon |
|---|---|---|
| pHSA140 | 5'-TTCGAAACG | 5'-AGGAATTC |
| pHSA413, pHSA313 | 5'-TTCGAAACG | 5'-NONE |

Several regulatory regions have been characterized and can be employed in conjunction with the expression of HSA in *Pichia pastoris*. Exemplary 5' regulatory regions are the primary alcohol oxidase (AOX1), dihydroxyacetone synthase (DAS1), and the p40 regulatory regions, derived from *Pichia pastoris* and the like. The presently preferred 5' regulatory regions employed in the practice of this invention are those characterized by their ability to respond to methanol-containing media, such regulatory regions selected from the group consisting of AOX1, and DAS1, disclosed by D. W. Stroman et al. in U.S. Pat. No. 4,855,231, incorporated herein by reference. The most preferred 5' regulatory region for the practice of this invention is the AOX1 5' regulatory region.

3' termination sequences should be utilized in the expression cassette as discussed above. 3' termination sequences may function to terminate, polyadenylate and/or stabilize the messenger RNA coded for by the structural gene when operably linked to a gene, but the particular 3' termination sequence is not believed to be critical to the practice of the present invention. A few examples of illustrative sources for 3' termination sequences for the practice of this invention include but are not limited to the *Hansenula polymorpha* and *Pichia pastoris* 3' termination sequences. Preferred are those derived from *Pichia pastoris* such as those selected from the group consisting of the 3' termination sequences of AOX1 gene, DAS1 gene, p40 gene and HIS4 gene. Particularly preferred is the 3' termination sequence of the AOX1 gene.

*Pichia pastoris* may be transformed with a variety of HSA structural genes (in the inventive transformants discussed herein the HSA structural gene encodes both a signal sequence and a mature HSA protein). HSA structural genes have been sequenced by Lawn et al. *Nuc. Acids Res.* 9:6105 (1981), and Dugaiczyk et al., *Proc. Natl. Acad. Sci. USA* 79:71 (1982). These genes may also be obtained by reisolation of the genes by the technique of Lawn et al., Dugaiczyk et al. or synthesized in vitro by a custom gene manufacturer such as British Biotechnology, Ltd. One possible method of obtaining a HSA gene would be to screen a human liver cDNA library with oligonucleotide probes or screen a human liver cDNA expression library with anti-HSA antisera to identify HSA expressing human liver cDNAs. One suitable HSA structural gene is provided in SEQ ID NO: 3 (nucleic acid) and SEQ ID NO: 4 (its corresponding amino acid sequence). Once a structural gene for HSA is recovered, it may be necessary to further tailor the gene. Following the isolation of a HSA structural gene, the gene is inserted into a suitable *Pichia pastoris* vector such as a plasmid or linear site-specific integrative vector.

Plasmid type vectors have long been one of the basic elements employed in recombinant DNA technology. Plasmids are circular extra-chromosomal double-stranded DNA found in microorganisms. Plasmids have been found to occur in single or multiple copies per cell. Included in plasmid DNA is the information required for plasmid reproduction, e.g. an autonomous replication sequence such as those disclosed by James M. Cregg in U.S. Pat. No. 4,837,148, issued Jun. 6, 1989, incorporated herein by reference. The autonomous replication sequences disclosed by Cregg provide a suitable means for maintaining plasmids in *Pichia pastoris*. Additionally one or more means of phenotypically selecting the plasmid in transformed cells may also be included in the information encoded in the plasmid.

Suitable integrative vectors for the practice of the present invention are the linear site-specific integrative vectors described by James M. Cregg, in U.S. Pat. No. 4,882,279, issued Nov. 21, 1989, which is incorporated herein by reference. These vectors comprise a serially arranged sequence of at least 1) a first insertable DNA fragment; 2) a selectable marker gene; and 3) a second insertable DNA fragment. An expression cassette containing a heterologous structural gene is inserted in this vector between the first and second insertable DNA fragments either before or after the marker gene. Alternatively, an expression cassette can be formed in situ if a regulatory region or promoter is contained within one of the insertable fragments to which the structural gene may be operably linked.

The first and second insertable DNA fragments are each at least about 200 nucleotides in length and have nucleotide sequences which are homologous to portions of the genomic DNA of the species to be transformed. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are oriented in the parent genome.

Nucleotide sequences useful as the first and second insertable DNA fragments are nucleotide sequences which are homologous with separate portions of the native genomic site at which genomic modification is to occur. For example, if genomic modification is to occur at the locus of the alcohol oxidase gene, the first and second insertable DNA fragments employed would be homologous to separate portions of the alcohol oxidase gene locus. Examples of nucleotide sequences which could be used as first and second insertable DNA fragments are deoxyribonucleotide sequences selected from the group consisting of the *Pichia pastoris* alcohol oxidase (AOX1) gene, dihydroxyacetone synthase (DAS1) gene, p40 gene and HIS4 gene. The AOX1 gene, DAS1 gene, p40 gene and HIS4 genes are disclosed in U.S. Pat. Nos. 4,855,231 and 4,885,242 both incorporated herein by reference. The designation DAS1 is equivalent to the DAS designation originally used in U.S. Pat. Nos. 4,855,231 and 4,885,242.

The first insertable DNA fragment may contain an operable regulatory region which may comprise the regulatory region utilized in the expression cassette. The use of the first insertable DNA fragment as the regulatory region for an expression cassette is a preferred embodiment of this invention. FIG. 1 provides a diagram of a vector utilizing the first insertable DNA fragment as a regulatory region for a cassette. Optionally, as shown in FIG. 1, an insertion site or sites and a 3' termination sequence may be placed immediately 3' to the first insertable DNA fragment. This conformation of the linear site-specific integrative vector has the additional advantage of providing a ready site for insertion of a structural gene without necessitating the separate addition of a compatible 3' termination sequence.

If the first insertable DNA fragment does not contain a regulatory region, a suitable regulatory region will need to be inserted linked to the structural gene, in order to provide an operable expression cassette. Similarly, if no 3' termination sequence is provided at the insertion site to complete the expression cassette, a 3' termination sequence can be operably linked to the 3' end of the structural gene.

It is also highly desirable to include at least one selectable marker gene in the DNA used to transform the host strain. This facilitates selection and isolation of those organisms which have incorporated the transforming DNA. The marker gene confers a phenotypic trait to the transformed organism which the host did not have, e.g., restoration of the ability to produce a specific amino acid where the untransformed host strain has a defect in the specific amino acid biosynthetic pathway, or provides resistance to antibiotics and the like. Exemplary selectable marker genes may be selected from the group consisting of the HIS4 gene (disclosed in U.S. Pat. No. 4,885,242) and the ARG4 gene (disclosed in U.S. Pat. No. 4,818,700 incorporated herein by reference) from *Pichia pastoris* and *Saccharomyces cerevisiae*, the invertase gene (SUC2) (disclosed in U.S. Pat. No. 4,857,467 incorporated herein by reference) from *Saccharomyces cerevisiae*, or the G418$^R$/kanamycin resistance gene from the *E. coli* transposable elements Tn601 or Tn903.

Those skilled in the art recognize that additional DNA sequences can also be incorporated into the vectors employed in the practice of the present invention, such as, for example, bacterial plasmid DNA, bacteriophage DNA, and the like. Such sequences enable the amplification and maintenance of these vectors in bacterial hosts.

The insertion of the HSA structural gene into suitable vectors may be accomplished by any suitable technique which cleaves the chosen vector at an appropriate site or sites and results in at least one operable expression cassette containing the HSA structural gene being present in the vector. Ligation of the HSA structural gene may be accomplished by any appropriate ligation technique such as utilizing T4DNA ligase.

The initial selection, propagation, and optional amplification of the ligation mixture of the HSA structural gene and a vector is preferably performed by transforming the mixture into a bacterial host such as *E. coli* (although the ligation mixture could be transformed directly into a yeast host but, the transformation rate would be extremely low). Suitable transformation techniques for *E. coli* are well known in the art. Additionally, selection markers and bacterial origins of replication necessary for the maintenance of A vector in a bacterial host are also well known in the art. The isolation and/or purification of the desired plasmid containing the HSA structural gene in an expression system may be accomplished by any suitable means for the separation of plasmid DNA from the host DNA. Similarly the vectors formed by ligation may be tested, preferably after propagation, to verify the presence of the HSA gene and its operable linkage to a regulatory region and a 3' termination sequence. This may be accomplished by a variety of techniques including but not limited to endonuclease digestion, gel electrophoresis, or Southern hybridization.

Transformation of plasmids or linear vectors into yeast hosts may be accomplished by suitable transformation techniques including but not limited to those taught by Cregg and Barringer, U.S. Pat. No. 4,929,555; Hinnen et al., *Proc. Natl. Acad. Sci.* 75, (1978) 1929; Ito et al., *J. Bacteriol.* 153, (1983) 163; Cregg et al. *Mol. Cell Biol.* 5 (1985), pg. 3376; D. W. Stroman et al., U.S. Pat. No. 4,879,231, issued Nov.

7, 1989; or Sreekrishna et al., Gene, 59 (1987), pg. 115. Preferable for the practice of this invention is the transformation technique of Cregg et al. (1985). It is desirable for the practice of this invention to utilize linear vectors and select for insertions by Southern hybridization.

The yeast host for transformation may be any suitable methylotrophic yeast. Suitable methylotrophic yeasts include but are not limited to yeast capable of growth on methanol selected from the group consisting of the genera Hansenula and Pichia. A list of specific species which are exemplary of this class of yeasts may be found in C. Anthony, *The Biochemistry of Methylotrophs,* 269 (1982). Presently preferred are methylotrophic yeasts of the genus Pichia such as the auxotrophic *Pichia pastoris* GS115 (NRRL Y-15851); *Pichia pastoris* GS190 (NRRL Y-18014) disclosed in U.S. Pat. No. 4,818,700; and *Pichia pastoris* PPF1 (NRRL Y-18017) disclosed in U.S. Pat. No. 4,812,405. *Auxotrophic Pichia pastoris* strains are also advantageous to the practice of this invention for their ease of selection. It is recognized that wild type *Pichia pastoris* strains (such as NRRL Y-11430 and NRRL Y-11431) may be employed with equal success if a suitable transforming marker gene is selected, such as the use of SUC2 to transform *Pichia pastoris* to a strain capable of growth on sucrose or an antibiotic resistance marker is employed, such as resistance to G418.

Transformed *Pichia pastoris* cells can be selected for by using appropriate techniques including but not limited to culturing previously auxotrophic cells after transformation in the absence of the biochemical product required (due to the cell's auxotrophy), selection for and detection of a new phenotype ("methanol slow"), or culturing in the presence of an antibiotic which is toxic to the yeast in the absence of a resistance gene contained in the transformant.

Isolated transformed *Pichia pastoris* cells are cultured by appropriate fermentation techniques such as shake flask fermentation, high density fermentation or the technique disclosed by Cregg et al. in, *High-Level Expression and Efficient Assembly of Hepatitis B Surface Antigen in the Methylotrophic Yeast, Pichia Pastoris* 5 Bio/Technology 479 (1987). Isolates may be screened by assaying for HSA production to identify those isolates with the highest HSA production level.

Transformed strains, which are of the desired phenotype and genotype, are grown in fermentors. For the large-scale production of recombinant DNA-based products in methylotrophic yeast, a three stage, high cell-density, batch fermentation system is normally the preferred fermentation protocol employed. In the first, or growth stage, expression hosts are cultured in defined minimal medium with an excess of a non-inducing carbon source (e.g. glycerol). When grown on such carbon sources, heterologous gene expression is completely repressed, which allows the generation of cell mass in the absence of heterologous protein expression. It is presently preferred, during this growth stage, that the pH of the medium be maintained at about 5. Next, a short period of non-inducing carbon source limitation growth is allowed to further increase cell mass and derepress the methanol responsive promoter. The pH of the medium during this limitation growth period is adjusted to the pH value to be maintained during the production phase, which is generally carried out at about pH 5 to about pH 6, preferably either about pH 5.0 or about pH 5.8. Subsequent to the period of growth under limiting conditions, methanol alone (referred to herein as "limited methanol fed-batch mode") or a limiting amount of non-inducing carbon source plus methanol (referred to herein as "mixed-feed fed-batch mode") are added in the fermentor, inducing the expression of the heterologous gene driven by a methanol responsive promoter. This third stage is the so-called production stage.

The invention will now be described in greater detail in the following non-limiting examples.

EXAMPLES

General information pertinent to the Examples:

Strains

*Pichia pastoris* GS115 (his 4) NRRL Y-15851

*E. coli* JM103 delta (lac pro) thi rpsl (strA) supE endA sbcB hsdR.

*E. coli* K12 MC1061 NRRl-18016 (F−, araD139 delta (lac 1POZY)×74 galk galu hsr hsm(+) rpsL delta (araABOIC leu)7697.

*E. coli* DG75' (hsd1, leu6, lacY, thr−1, supE44, tonA21, lambda−)

Buffers, Solutions and Media

The buffers, solutions, and media employed in the following examples have the compositions given below:

| | |
|---|---|
| dH$_2$O | deionized H$_2$O that has been treated with a milli-Q (Millipore) reagent water system. |
| 1M Tris buffer | 121.1 g Tris base in 800 mL of H$_2$O; adjust pH to the desired value by adding concentrated (35%) aqueous HCl; allow solution to cool to room temperature before final pH adjustment, dilute to a final volume of 1 L. |
| TE buffer | 1.0 mM EDTA in 0.01 M (pH 8.0) Tris bufffer |
| SED | 1 M sorbitol 25 mM EDTA 50 mM DTT, added prior to use -adjust to pH 8 |
| SCE | 9.1 g sorbitol 1.47 g Sodium citrate 0.168 g EDTA -pH to 5.8 with HCl in 50 ml dH$_2$O and autoclave |
| CaS | 1 M sorbitol 10 mM CaCl$_2$ -filter sterilize |
| SOS: | 1 M sorbitol 0.3x YPD 10 mM CaCl$_2$ |
| PEG | 20% polyethylene glycol-3350 10 mM CaCl$_2$ 10 mM Tris-HCl (pH 7.4) -filter sterilize |
| Solution A | 0.2 M Tris-HCl (pH 7.5) 0.1 M MgCl$_2$ 0.5 M NaCl 0.01 M dithiothreitol (DTT) |
| Solution B | 0.2 M Tris-HCl (pH 7.5) 0.1 M MgCl$_2$ 0.1 M DTT |
| Solution C (keep on ice) | 4 µl solution B 4 µl 10 mM dATP 4 µl 10 mM dTTP 4 µl 10 mM dGTP 4 µl 10 mM dCTP 4 µl 10 mM ATP 5 µl T$_4$ ligase (2 U/µl) 12 µl H$_2$O, Recipe for Solution C was modified from Zoller & Smith |
| 20X SSPE | 4.4 g NaOH 7.4 g Na$_2$EDTA 27.6 g NaH$_2$PO$_4$.H$_2$O 210 g NaCl -pH adjusted to 7.5–8.0 with NaOH -H$_2$O to 1 liter |
| 50X Denhardt's | 5 g Ficoll 400 |

| | -continued |
|---|---|
| | 5 g Polyvinylpyrolidine |
| | 5 g BSA Fraction V |
| | H₂O to 500 ml |
| 20X SSC | 175.3 g NaCl |
| | 88.2 g sodium citrate |
| | -pH to 7.0 with NaOH |
| | -H₂O to 1 liter |
| LB Broth, 1 liter | 5.0 g yeast extract |
| | 10.0 g tryptone |
| | 5.0 g NaCl |
| 10X Transfer Buffer | 96.8 g Trizma Base |
| | 9.74 g glycine |
| | water to 1 liter |
| Transfer Buffer for Tank | 500 mls 10X Transfer Buffer |
| | 1000 mls methanol |
| | 3500 mls water |
| Western Buffer- for 1 liter | 2.5 g gelatin put in solution by microwaving first in 100 mls water |
| | 100 mls 10X PBS |
| | 1 ml 50% Tween-20 |
| | 4 mls 5% sodium azide |
| | dH₂O to 1 liter |
| Coating Buffer | 0.160 g Na₂CO3 (sodium carbonate) |
| | 0.294 g NaHCO3 (sodium carbonate) |
| | Add distilled water to 100 ml. Do not pH. (pH should be 9.5) |
| Tris Buffered Saline (TBS) | 26.1 g NaCl |
| | 2.63 g Tris |
| | Add distilled water to 3 liters. |
| | Adjust pH to 7.5 with HCl. |
| Tris Buffeted Saline/Tween (TBST) | 1 liter of TBS |
| | 2.5 ml of 20% Tween-20 |
| Blotto Buffer | 50 g of non-fat dry milk (Carnation) |
| | 1 g thimerosal (Sigma) |
| | 100 µl of antifoam (Sigma, 30% emulsion) |
| | 2.5 ml of 20% Tween-20 |
| | 100 ml 10x PBS (house stock) |
| | Add distilled water to 1 liter |
| | Adjust pH to 7.5 |
| Ligation Buffer | 50 mM Tris-HCl (pH 7.4) |
| | 10 mM MgCl₂ |
| | 10 mM dithiothreitol |
| | 1 mM ATP |
| Phosphatase Buffer | 50 mN Tris-HCl (pH 9.0) |
| | 1 mM MgCl₂ |
| | 1 mM ZnCl₂ |
| | 1 mM spermidine |
| Bsu36Ibuffer | 100 mM NaCl |
| | 10 mM Tris-HCl (pH 7.4) |
| | 10 mM MgCl₂ |
| | 100 µg/ml BSA |
| Csp45Ibuffer | 60 mM NaCl |
| | 10 mM Tris-HCl, pH 7.5 |
| | 7 mM MgCl₂ |
| | 100 µg/ml BSA |
| REact 1 buffer | 50 mM Tris-HCl, pH 8.0 |
| | 10 mM MgCl₂ |
| | 100 µg/ml BSA |
| REact 2 buffer | REact 1 buffer + 50 mM NaCl |
| REact 3 buffer | REact 1 buffer + 100 mM NaCl |
| HS buffer | 50 mM Tris-HCl, pH 7.5 |
| | 10 mM MgCl₂ |
| | 100 mM NaCl |
| | 1 mM DTT |
| | 100 µg/ml BSA |
| 10X Basal Salts | 42 mls Phosphoric Acid, 85% |
| | 1.8 g Calcium Sulfate.2H₂O |
| | 28.6 g Potassium Sulfate |
| | 23.4 g Magnesium Sulfate.7H₂O |
| | 6.5 g Potassium Hydroxide |
| Ptm₁ Trace Salts Solution | 6.0 g Cupric Sulfate.5H₂O |
| | 0.08 g Sodium Iodide |
| | 3.0 g Manganese Sulfate.H₂O |
| | 0.2 g Sodium Molybdate.H₂O |
| | 0.02 g Boric Acid |
| | 0.5 g Cobalt Chloride |
| | 20.0 g Zinc Chloride |
| | 65.0 g Ferrous Sulfate.H₂O |
| | 0.20 g Biotin |
| | 5.0 mls Sulfuric Acid |

| | -continued |
|---|---|
| YPD (yeast extract peptone dextrose medium) | 10 g bacto yeast extract |
| | 20 g peptone |
| | 10 g dextrose |
| | water to 1 liter |
| MGY (minimal glycerol medium) | 13.4 g yeast nitrogen base with ammonium sulfate, and without amino acids |
| | 400 µg biotin |
| | 10 ml glycerol |
| | water to 1 liter |
| MM (minimal methanol medium) | Same as MGY, except that 5 ml methanol is used in the place of 10 ml glycerol. |
| SDR (supplemented dextrose regeneration medium): | 13.4 g yeast nitrogen base with ammonium sulfate and without amino acids |
| | 400 µg biotin |
| | 182 g sorbitol |
| | 10 g glucose |
| | 2 g Histidine assay mix (Gibco) |
| | 50 mg glutamine |
| | 50 mg methionine |
| | 50 mg lysine |
| | 50 mg leucine |
| | 50 mg isoleucine |
| | 10 g agarose |
| | water to 1 liter |
| BMGR (Buffered minimal glycerol-enriched medium) | 100 ml/liter Potassium phosphate buffer, (pH 6.0) |
| | 13.4 grams/liter Yeast nitrogen base with ammonium sulfate |
| | 400 µg/liter biotin |
| | 10 ml/liter glycerol |
| Amino acids | glutamic acid, methionine, lysine, leucine and isoleucine: each at 5 mg/liter; |
| | all the other amino acids except histidine at 1 mg/liter |
| Nucleotides | adenine sulfate, guanine hydrochloride, uracil, and xanthine, each at 40 µg/liter |
| Vitamins | thiamine hydrochloride, riboflavin, and calcium pantothenate, each at 2 µg/liter; |
| | pyridoxide hydrochloride and nicotinic acid, each at 4 µg/liter; |
| | pyridoxamine hydrochloride and pyridoxal hydrochloride, each at 1 µg/liter; |
| | para-amino benzoic acid at 0.3 µg/liter; |
| | folic acid at 0.03 µg/liter |
| Trace minerals | magnesium sulfate at 800 µg/liter; |
| | ferrous sulfate at 40 µg/liter; |
| | manganese sulfate at 80 µg/liter; |
| | sodium chloride at 40 µg/liter |
| BMGY (Buffered minimal glycerol-complex medium) | 100 ml/liter potassium phosphate buffer, (pH 6.0) |
| | 13.4 grams/liter yeast nitrogen base with ammonium sulfate and without amino acids |
| | biotin at 400 µg/liter |
| | glycerol at 10 ml/liter |
| | yeast extract at 10 g/liter |
| | peptone at 20 g/liter |
| BMMR (Buffered minimal methanol-enriched medium) | Same as BMGR, with the exception that 5 ml methanol/liter is added in the place of glycerol |
| BMMY (Buffered minimal methanol-complex medium) | Same as BMGY, with the exception that 5 ml methanol/liter is added in the place of glycerol |

Techniques

Suitable techniques for recombinant DNA lab work may be found in many different references including but not limited to: *Methods in Enzymology*, (Orlando, Fla.: Academic Press, Inc.), particularly Volume 152, published as, *Guide to Molecular Cloning Techniques*, by Berger and Kimmel (Orlando, Fla.: Academic Press, Inc., 1987) and *Molecular Cloning/A Laboratory Manual*, by Sambrook et al., 2d ed. (Cold Spring Harbor Laboratory Press, 1989) and which are all hereby incorporated by reference.

Example I

Construction of mHSA13

Mutagenesis of HSA Structural Gene Insert

DNA encoding HSA was obtained from pHSA13, disclosed in European Pat. No. Application 0 344 459, herein incorporated by reference, by EcoRI digestion. A 2069 bp fragment was recovered by electrophoresis on a 1% agarose gel. The DNA was mutagenized by the following procedure to make the following changes: 1) an EcoRI restriction site was added immediately prior to the ATG of the HSA signal sequence, and 2) an EcoRI restriction site was added immediately adjacent to the TAA stop codon in the HSA cDNA.

The oligonucleotides employed in the mutagenesis were:
1) 5' mutagenesis to add EcoRI site, mutagenizing nucleotide sequence: 5' CCC TCA CAC GCC TTT GAA TTC ATG AAG TGG GTA ACC 3' (SEQ ID NO:5) (nucleic acid) and SEQ ID NO: 6 (its corresponding amino acid sequence starting from the ATG start codon)
2) 3' mutagenesis to add EcoRI site, mutagenizing nucleotide sequence: 5' GCC TTA GGC TTA TAA GAA TTC AGT TTA AAA GCA TCT CAG 3' (SEQ ID NO:7) (nucleic acid) and SEQ ID NO: 8 (its corresponding amino acid sequence translated from the 5' end of SEQ ID NO: 7 to the TAA termination codon)

and were synthesized using an Applied Biosystems DNA Synthesizer, Model 380A using cyanoethylphosphoramidite chemistry.

1.2 μg of double-stranded m13mp10 were digested with EcoRI and dephosphorylated and ligated with 450 ng of the previously isolated 2069 bp fragment containing the HSA structural gene.

The ligation mixture was transformed into competent JM103 cells (competent JM103 were prepared as described in Example II for MC1061 cells). The mixture was then plated on LB media containing IPTG and X-gal and the plates screened for clear plaques. DNA was recovered from transformants and digested with Hind III. The correct phage demonstrated bands of 7369 and 1950 bp and was called mHSA13.

A. A large scale miniprep was performed on positive plaques which had been incubated for approximately 7 hours in 2 mls of L media. 25 mls of LB media was inoculated with 250 μl of freshly grown JM103 cells. The culture was grown for 1 hour and inoculated with 100 μl of the 7 hour old plaque culture. The culture was then grown overnight. The culture was centrifuged twice at 10,000 rpms for 10 minutes on a Sorvall RC-5B rotor SS34 to clear the supernatant. 3.5 ml of 20% PEG/2.5M NaCl was added to the culture and it was incubated for 5 hours at 4° C. The culture was then centrifuged again as above for 10 minutes. The supernatant was discarded and the pellet was resuspended in 2 mls of TE buffer. The pellet was then extracted with phenol, equilibrated with TE, extracted with phenol/chloroform, extracted twice with CHCl₃ and once with ether. 8M LiCl was added to attain a final concentration of 0.8M. 3 volumes of ethanol were added and the solution left overnight at −20° C. to precipitate the DNA present. The solution was next centrifuged for 10,000 rpms for 10 minutes as previously described and rinsed with 70% ethanol. The precipitate was resuspended in 150 μl of 10 mM Tris (pH 7.4).

B. One pmole of M13 recombinant template was mixed with 20 pmole of oligonucleotide 1 (for 5' mutagenesis to create an EcoRI site), 1 μl of solution A and dH₂O was added to give a final volume of 10 μl. The sample was incubated at 65° C. for 5 minutes, and the temperature was then reduced to 37° C. for 30 minutes.

C. The following was then added to the sample:

| | |
|---|---|
| Solution B | 1 μl |
| 10 mM dATP | 1 μl |
| 10 mM dCTP | 1 μl |
| 10 mM dGTP | 1 μl |
| 10 mM dTTP | 1 μl |
| 5 u/μl Klenow | 2 μl |
| dH₂O | 3 μl |
| | 20 μl | and allowed to incubate at 15° C. for at least 4–6 hours.

D. The sample was then diluted 1:40 with dH₂O. 5 μl was used to transform 6 tubes of competent JM103 cells (200 μl each). The transformed JM103 cells were plated on rich media in a soft agar overlay.

E. The positive plaques were then screened for by filter hybridization.

A hybridization probe of 15 pmole of complementary oligonucleotide in a total volume of 25 μl total volume was heated to 65° C. for 10 minutes. 3 μl 10× kinase buffer (Maniatis), 1 μl γ-ATP and 1 μl polynucleotide kinase (100 u/μl) were added to the sample. The sample was incubated for 1 hour at 37° C. and run through G-50 fine Sephadex. The first peak off the column was collected.

Nitrocellulose filters were prepared for hybridization with the above probe by placing and orienting the filters on the transformation plates for 5–10 minutes. The filters were then removed from the plates and floated on a denaturing solution (1.5M NaCl, 0.5N NaOH) for 3 minutes with the backside on top of the solution. The filters were then submerged in the denaturing solution for 5 minutes. The nitrocellulose filters were transferred to a neutralizing solution (1M Tris./HCl, pH 8; 1.5M NaCl) for 5 minutes. The neutralized filter was then transferred to 2× SSC (1× SSC is 150 mM NaCl, 15 mM NaCitrate) for 5 minutes. The filter was then air dried and baked for 1 hour at 80° C. under a vacuum. The filters were prehybridized for 1 hour at 65° C. in a sealed plastic bag containing 5 ml of hybridization buffer filter, 10× Denhardts (1× Denhardts is 0.02% Ficoll, 0.02% polyvinyl pyrrolidone, 0.02% bovine serum albumin) 0.5% SDS and 5× SSPE. The hybridization buffer was replaced with 5 ml/filter of fresh hybridization buffer. The screening oligonucleotides utilized were as follows:
1) 5' mutagenesis the screening oligonucleotide was 5' GCC TGG GAA TTC ATG AAG 3' (SEQ ID NO:9) (nucleic acid) and SEQ ID NO: 10 (its corresponding amino acid sequence starting from the ATG start codon)
2) 3' mutagenesis the screening oligonucleotide was 5' TTA TAA GAA TTC AGT TTA 3' (SEQ ID NO:11) (nucleic acid) and SEQ ID NO: 12 (its corresponding amino acid sequence translated from the 5' end of SEQ ID NO: 11 to the TAA termination codon)

The previously prepared screening oligonucleotide was first incubated at 65° C. for 5 minutes, and then enough probe was added to the fresh hybridization buffer containing the filter to give 1×10⁶ cpm/ml. Hybridization was performed at 5° C. below the calculated melting temperature of the probe for 4 hours.

The filters were then washed three times for 10 minutes each with 6× SSC at room temperature. The filters were finally washed one time with 6× SSC at the hybridization temperature. The filters were placed on a 3 MM Whatman paper to dry, and then exposed to film (marked for orientation) overnight.

Three positive plaques were each picked and grown separately in 2 mls of LB broth at 37° C. for 5 hours.

F. Mini template preps were performed on each of these positive plaques.

One ml of the plaque culture was transferred into an Eppendorf tube and centrifuged for 5 minutes in a Eppendorf Model 5414 Centrifuge. 800 μl of the supernatant was recovered and 200 μl of 20% PEG with 2.5M NaCl was added thereto. The supernatant was incubated at room temperature for 10 minutes. The supernatant was centrifuged for 10 minutes in the Eppendorf centrifuge previously used. The supernatant was removed by aspiration and the pellet formed by centrifuging was redissolved in 200 μl TE (10 mM Tris, pH 7.4; 1 mM EDTA). The redissolved pellet was then phenol/chloroform extracted and the template DNA in the upper aqueous phase was precipitated by the addition of a LiCl solution until a 0.8M concentration was reached. To the solution was added 2 ½–3 volumes of ethanol and precipitated on dry ice for 5 minutes. The precipitate was centrifuged for 10 minutes in the previously mentioned Eppendorf centrifuge. The final volume was brought up to 150 μl with TE.

G. 200 μl of competent JM103 cells were transformed with the recovered DNA. 1 μl and 1 μl of a 1/10 dilution of the isolated phase DNA was used in the transformation.

H. The transformation mixture was plated and plaques were screened with oligonucleotides as previously described in step E.

I. A large scale miniprep was performed on positive plaques which had been incubated for approximately 7 hours in 2 mls of L media. 25 mls of LB media was inoculated with 250 μl of freshly grown JM103 cells. The culture was grown for 1 hour and inoculated with 100 μl of the 7 hour old plaque culture. The culture was then grown overnight. The culture was then centrifuged twice at 10,000 rpms for 10 minutes on a Sorvall RC-5B rotor SS34 to clear the supernatant. 3.5 ml of 20% PEG/2.5M NaCl was added to the culture and it was incubated for 5 hours at 4° C. The culture was then centrifuged again as above for 10 minutes. The supernatant was discarded and the pellet was resuspended in 2 mls of TE buffer. The pellet was then extracted with phenol, equilibrated with TE, extracted with phenol/chloroform extracted twice with $CHCl_3$ and once with ether. 8M LiCl was added to attain a final concentration of 0.8M LiCl. 3 volumes of ethanol were added and the solution left overnight to precipitate the DNA present. The solution was next centrifuged for 10,000 rpms for 10 minutes as previously described and rinsed with 70% ethanol. The precipitate was resuspended in 150 μl of 10mM Tris (pH 7.4).

J. The positive plaques were then sequenced by dideoxy sequencing to find the M13 constructs with the correct mutations.

K. Repeat steps B–J using M13 constructs with the correct 5' mutations as templates and the second oligonucleotide as a primer for 3' mutagenesis. The correct mutation was designated mHSA140.

L. Recover RF DNA of mHSA140 using the alkaline lysis method of Maniatis.

Example II

Construction of the pHSA140 Expression Vectors pA0804 is available in an *E. coli* host from the Northern Regional Research Center of the United States Department of Agriculture, Peoria, Ill., accession number B-18114. pA0804 is recovered by isolating the plasmid DNA, digesting with EcoRI, gel electrophoresing to recover the ~7.5 kb fragment, which is linear pA0804 cut at its unique EcoRI site.

pA0804 is a vector capable of site-specific disruption of the *Pichia pastoris* AOX1 locus. It contains the following elements: the AOX1 promoter and transcription terminator separated by a unique EcoRI cloning site; the wild-type Pichia HIS4 gene; a genomic segment of DNA from the 3' end of the AOX1 locus downstream of the transcription terminator; and sequences necessary for selection and replication in a bacterial host. The components are arranged such that a BglII restriction digest of the plasmid releases a DNA fragment containing the expression cassette and selective marker whose ends are homologous to a continuous portion of the genome, the AOX1 locus, and can be stably inserted into the chromosome during transformation. Additionally the ampicillin resistance gene and the ori from plasmid pBR322 are also contained in the pA0804 plasmid.

A vector containing the gene coding for the production of HSA was constructed from pA0804 and mHSA140. pA0804 was digested with EcoRI and the ends were dephosphorylated by treatment with alkaline phosphatase (1 U enzyme at 37° C. for 1 hr. in 50 mM Tris.Cl, pH 9.0, 1 mM $MgCl_2$, 100 mM $ZnCl_2$, 1 mM spermidine). mHSA140 was also digested with EcoRI, and a 1829 bp fragment encoding HSA was released. This fragment was purified using 0.8% preparative agarose gel electrophoresis. 60 ng of the fragment were ligated to 240 ng of pA0804 by incubation at 23° C. for 1 hr in 66 mM Tris.Cl, pH 7.4, 5 mM $MgCl_2$, 5 mM dithiothreitol, 1 mM ATP, with 1 Weiss Unit of T4 ligase in a 10 μl reaction volume. The ligation reaction was used to transform competent MC1061 cells to ampicillin resistance.

MC1061 was rendered competent for transformation in the following manner. A mid-log culture (50 ml) of *E. coli* MC1061 was harvested by centrifugation in an IEC DPR 600 clinical centrifuge at 3,000 rpm for 5 min at 4° C. and washed in 10 mM NaCl. The culture was resuspended in 25 ml of 50 mM $CaCl_2$ for 30 min at 0° C. The cells were centrifuged as above and resuspended in 2 ml of 50 mM CaCl 2.

For transformation, the ligation reaction was added to 200 μl of the competent cell suspension and incubated at 0° C. on ice for 15 minutes, heat shocked at 37° C. for 5 minutes and incubated at 23° C. for 5 minutes. The cells were plated directly onto LB agar plates containing 50 μg/ml ampicillin. The plates were incubated at 37° C. for 10–16 hours. The resulting colonies were $Amp^R$. The resistant colonies were harvested and characterized by restriction digestion. Cells were grown in 5 ml of L-broth containing 50 μg/ml ampicillin for 5 hr at 37° C. and DNA was prepared by the method of Birnboim and Doly [*Nucleic Acids Research* 7:1513 (1979)]. The minipreps displaying 4750, 3000 and 1900 bp fragments upon PvuII digestion were chosen and designated pHSA140.

Example III

Transformation of *Pichia pastoris*

*Pichia pastoris* strains containing the vectors described in Example II were generated in the following manner. Methanol utilization deficient ($Mut^-$ or methanol slow) and wild type methanol utilization ($Mut^+$ or metaanol normal) strains were developed.

*Pichia pastoris* strain GS115 (his4; NRRL Y-15851) was transformed using the spheroplast transformation technique described by Cregg et al., Bio/Technology 5:479–485 (1987). See also U.S. Pat. No. 4,879,231.

A. $Mut^+$ Strains

To direct integration of the vector to the AOX1 locus, 2 and 10 μg of Sac1-digested pHSA140 were separately transformed into 5 of $OD_{600}$ (or $25 \times 10^7$ cells) of GS115. Transformants were regenerated on minimal media and screened for the His$^+$ phenotype. Several His$^+$ transformants were then screened by Southern analysis for the site of integration and vector copy number (Example V).

B. Mut$^-$ Strains

To develop Mut$^-$ strains, in which the HSA expression cassette inegrates into and disrupts the AOX1 structural gene, vector pHSA140 was digested with PvuI and then partially digested with BglII. The digest was then size fractionated on a 0.8% agarose gel and DNA in the size range of 6.0–9.0 kb was isolated (the expression cassette was expected to be ~7.4 kb). 5 μg of this DNA were used to transform 5 $OD_{600}$ ($25 \times 10^7$ cells) of GS115 by the spheroplast method. His$^+$ cells were identified and then screened for the Mut$^-$ phenotype as follows.

Transformants were pooled by scraping the surface of the plate in the presence of sterile distilled water and sonicated at low output for 15 seconds. They were subsequently diluted to an $A_{600}$=0.1 and plated at dilutions of $10^{-3}$ and $10^{-4}$, in duplicate onto minimal plates containing glycerol as the carbon source, and incubated at 30° C. for 2–3 days. They were then replica-plated onto minimal plates to which 100 μl of methanol was added in the vapor phase. After a 24-hour incubation at 30° C., it was apparent that 4% of the transformants were growing more slowly on methanol than the rest of the transformants. Five of the His$^+$ Mut$^-$ isolates were examined by Southern analysis (Example V).

Example IV

Yeast DNA Miniprep $10^4$ cells/ml were seeded in 5 ml YPD at 30° C. overnight and then pelleted using a Damon IEC DPR600 clinical centrifuge at 3,000 rpm for 5 minutes. The pellet was resuspended in 0.5 ml of 1M sorbitol, 0.1 ml 0.5M EDTA, pH 8 and the sample transferred to a 1.5 ml microfuge tube. 0.02 ml of 2.5 mg/ml Zymolyase 100,000 (Miles Laboratories) was added, and the sample was incubated at 37° C. for 60 minutes. The cells were pelleted using the microfuge for 1 minute at high speed, and resuspended in 0.5 ml of 50 mM Tris.Cl, pH 7.4 and 20 mM EDTA. 0.05 ml of 10% SDS was added, the sample mixed, and incubated at 65° C. for 30 minutes. 0.2 ml of 5M potassium acetate, pH 5.2, was added and the sample was incubated on ice for 60 minutes. The sample was again spun in a microfuge at high speed for 5 minutes.

The supernatant was transferred to a fresh 1.5 ml microfuge tube and 1 volume of isopropanol at room temperature was added. The sample was mixed and allowed to sit at room temperature for 5 minutes, then spun very briefly (10 seconds) in a microfuge at high speed. The supernatant was poured off and the pellet air dried. After resuspending the pellet in 0.3 ml of 10 mM Tris.Cl, pH 7.4 and 1 mM EDTA, 15 μl of a 1 mg/ml solution of pancreatic RNase was added, and the sample was incubated at 37° C. for 30 minutes. 0.03 ml of 3M sodium acetate was added, the sample mixed, and 0.2 ml of isopropanol added. The sample was spun in a microfuge at high speed to pellet the DNA. The supernatant was then poured off, the pellet dried and resuspended in 0.1–0.3 ml of 10 mM Tris.Cl, pH 7.4 and 1 mM EDTA. (Note: Before using the DNA in a restriction digest, it may be necessary to spin the solution for 15 minutes at high speed in the microfuge to remove any insoluble material which may inhibit the digestion).

Example V

Strain Characterization

DNA was prepared from the transformed Pichia cells (Example III) and from untransformed host Pichia cells as described in Example IV, and digested with EcoRI. The samples were electrophoresed on 0.8% agarose gels, and Southern blots were performed (Maniatis et al., 1982). The filters were hybridized with an AOX1 specific probe or with a HIS4 specific probe to determine where integration had occurred. The site of integration was determined by comparing the spectrum of hybridization of a given transformant with the wild type strain. Any alteration in the size of the wild type band was evidence of integration at that locus. A summary of the Southern hybridizations and strain characterization for the strains chosen for further analysis is below.

TABLE I

| Strain Name | Site of Integration | Vector Copy Number |
| --- | --- | --- |
| G + HSA140S1 | AOX1 | one |
| G + HSA140S4 | AOX1 | two |
| G + HSA140S3 | AOX1 | >two |
| G − HSA140S1 | AOX1 | one |

Fermentor Growth of HSA-Expressing Pichia Strains

Inocula were prepared from selective plates and grown overnight at 30° C. in buffered YNB containing 2% glycerol to an $OD_{600}$ of 0.5–10.0. An aliquot of 5–50 ml of the overnight culture was added to a 2-liter capacity fermentor, and the repressed growth phase continued in 5× basal salts containing 5 ml/L of $PTM_1$ salts at 30° C. The pH was maintained at 5.0 by the addition of 40% (v/v) ammonium hydroxide, and foaming was controlled by the addition of 5% (v/v) Struktol antifoam. Dissolved oxygen was maintained above 20% by increased aeration and agitation as needed. The temperature was maintained at about 30° C. This batch growth phase continued for 20–30 hours until the glycerol was exhausted. The fermentation was then continued in either a methanol-limited fed-batch mode for Mut$^+$ strains or a methanol-excess fed-batch mode for Mut$^-$ strains.

a. Mut$^+$ fermentation; methanol-limited fed batch

Run 544: G+HSA140S1 (1 copy)

Run 557: G+HSA140S4 (2 copy)

Run 545: G+HSA140S3 (>2 copy)

In order to continue building cell density as well as to prevent the accumulation of excess ethanol in the fermentor, the AOX1 promoter was derepressed to allow the expression of a small amount of alcohol oxidase before induction by the addition of methanol. This derepression was achieved by growth under glycerol-limited conditions at about pH 5.0. Following exhaustion of the glycerol in the initial growth phase, a 50% (w/v) glycerol feed (containing 12 ml/L of $PTM_1$ trace salts) was initiated at a rate of 8–16 ml/hour and continued until approximately 120–140 ml had been added. Full expression of the AOX1 promoter was then induced by the initiation of a methanol feed (100% MeOH plus 12 ml/L $PTM_1$ trace salts) at 1 ml/hour. The methanol feed was maintained for several hours until the culture responded to methanol limitation. This response was expressed as a sudden rise in dissolved oxygen upon a brief cessation of the methanol feed. The methanol feed was then increased over an 8–12 hour period until a rate of 5.5 ml/hour was achieved. Fermentation was continued under these conditions for 82, 96 or 98 hours on methanol before the culture was harvested.

b. Mut$^-$ fermentation; methanol excess fed batch

The Mut$^-$ fermentations were conducted as described for the Mut$^+$ fermentations, except the MeOH feed was increased after 4 hours of 1 ml/hr feed to 3-4 ml/hr, to give a residual methanol concentration less than 0.5%.

Quantification of HSA Secreted into Growth Media a. ELISA

The ELISA procedure for human serum albumin requires the following reagents: Human Albumin (obtained from Cappell, Organon Teknika), Goat anti-HSA antibody (obtained from Atlantic Antibodies), Goat anti-HSA antibody, peroxidase conjugated (obtained from Cappell, Organon Tecknika), and O-phenylenediamine (OPD), dichloride salt (obtained from Sigma, 10 mg/tablet). The HSA was reconstituted following the manufacturer's directions. In this case (lot #26706) 3.0 ml of distilled water was added to the contents of the vial (the final concentration was 18.8 mg/ml). 29 aliquots of 100 µl each were labeled and quickfrozen.

16 aliquots were formed by diluting 100 µl of 18.8 mg/ml with 1.780 ml PBS (final 1.0 mg/ml). The 16 aliquots of 100 µl were labeled and quickfrozen.

100 more aliquots were formed by diluting 100 µl of 1 mg/ml with 9.9 ml PBS (final 10 µl). The 100 aliquots of 100 µl each, were then labeled and quickfrozen. This dilution was used to begin the standard curve of dilutions. The goat anti-HSA was supplied in solution. The goat anti-HSA reagent was divided into 50 µl aliquots, labeled and quickfrozen. Goat anti-HSA conjugated to peroxidase was reconstituted by the addition of 2.0 mls of distilled water (final concentration 23 mg/ml). 50 µl of aliquots of the goat anti-HSA conjugate were then labeled and quickfrozen.

ELISA PROCEDURE

Note: Use buffers at room temperatures only

1. Make up coating buffer immediately before use. Dilute goat anti-HSA antibody 1:500. Add 200 µl of this solution to each well. Parafilm tightly and incubate one hour at 37° C.

2. Sharply flick contents of plate into sink. Wash 3 times with TBST. Wash 2 times with distilled water.

3. Add 200 µl blotto buffer to all wells. Parafilm tightly. Incubate overnight at 37° C.

4. Next morning, flick contents of wells into sink. Wash 3 times with TBST. Wash 2 times with distilled water.

5. Add 100 µl of TBST to all wells.

6. Dilute stock 10 µg/ml HSA standard with TBST.

S=stock from freezer=10 µg/ml

SS=substock=1:100 of S=10,000 pg/100 µl

S$^{-1}$=1:10 of SS=1,000 pg/100 µl

Dilute SS, 1:1=5,000 pg/100 µl

Dilute SS, 1:3.3=3,000 pg/100 µl

Dilute SS, 1:5=2,000 pg/100 µl

Dilute S$^{-1}$, 1:1=500 pg/100 µl

Dilute S$^{-1}$, 1:5=200 pg/100 µl

Dilute 3,000 pg/100 µl 1:1=1,500 pg/100 µl

8. Add 100 µl sample dilutions and standard curve dilutions to each well.

9. Parafilm tightly and incubate 2 hours at 37° C.

10. Wash five times with TBST. Wash two times with distilled water.

11. Dilute goat anti-HSA conjugate 1:2000 with blotto buffer. Incubate for two hours at room temperature in the dark.

12. Wash three times with TBST. Wash two times with distilled water.

13. Immediately before use: add one pellet of OPD to 3 mls of distilled water in a dark container. Pipet 21 mls of water into a 50 ml Falcon tube. Add 3 mls OPD solution to the Falcon tube, add 10 µl of 30% $H_2O_2$, and mix. Add 200 µl of this solution to each well. Parafilm tightly and incubate 10 minutes in the dark. Stop the reaction by addition of 50 µl 4.5M sulfuric acid.

14. Read on ELISA reader at 492 nm using filter 4.

b. Data

The level of HSA secreted from each of the strains, and other information pertinent to the fermentations, is provided in Table II:

TABLE II

Fermentation of HSA Strains

| Run | Strain | Copy Number | Integration Site | Hours on MeOH | Cell Density (Wet) g/l | HSA in Broth g/l |
|---|---|---|---|---|---|---|
| 537 | G − HSA140S1 | 1 | AOX1/Mut$^-$ | 98 | 445 | 0.971 |
| 544 | G + HSA140S1 | 1 | AOX1/Mut$^+$ | 96 | 415 | 0.964 |
| 557 | G + HSA140S4 | 2 | AOX1/Mut$^+$ | 82 | 450 | 0.754 |
| 545 | G + H5A140S3 | >2 | AOX1/Mut$^+$ | 96 | 353 | 0.185 |

Characterization of Recombinant Product a. Gel analysis

Samples of fermentation broths of fermentation runs 537, 544 and 545 were withdrawn at different time points during the induction phase and analyzed by SDS gels and Coomassie blue staining. 5 µl of a 10-fold dilution of fermentor broth (equivalent to 0.5 µl) were applied to the gel. The relative intensity of the stained bands of rHSA (recombinant HSA) and the HSA standard confirmed the high (gram/liter) rHSA levels found by ELISA. In addition, the rHSA from all three fermentations and at all time points analyzed showed identical mobility with the HSA standard (69 Kd). The fact that the rHSA was the major protein species secreted by all HSA expression strains suggests high initial purity (>90%) of the rHSA secreted into the growth medium. Another protein species which migrates at approximately 45 Kd could also be detected in increasing intensity with respect to fermentation time. This protein species may be produced in a secondary processing event during secretion or as a proteolytic product post-secretion by proteases secreted into the fermentation broth, or both. It is related to rHSA, as it was detectable on Western blots by HSA specific polyclonal antisera.

b. N-terminal sequence

Protein sequence of the N-terminal region of secreted rHSA was obtained on a dialysed sample of fermentor broth. The sequence was determined on an Applied Biosystems Model 470A protein sequencer. The phenylthiohydantoin (PTH) derivatives of the amino acids were identified by high performance liquid chromatography with an Applied Biosystems Model 120A analyzer. The results showed that the rHSA N-terminus is aspartic acid, consistent with the N-terminal amino acid of HSA. There does not appear to be any other precursor type of rHSA. The balance of the sequence determined was identical to the known sequence for HSA.

Example VI

Construction of HSA expression vector pHSA313

The pHSA313 vector was constructed to provide a vector with an exact linkage between the 3' end of the native AOX1

5' regulatory region (promoter) and the start codon of the HSA structural gene.

A. Creation of pHSA113ΔCla

About 200 ng of pHSA113 (disclosed in European Patent Application 0 344 459 and shown in FIG. 7) was digested at 37° C. for 1 hour with 1 unit of ClaI in 20 μl of REact 1 buffer. The digestion mixture was brought to 100 μl with water and extracted once with an equal volume of phenol:chloroform:isoamyl alcohol (25:24:1 V/V), followed by extracting the aqueous layer with an equal volume of chloroform:isoamyl alcohol (24:1). The DNA in the aqueous phase was precipitated by adjusting the NaCl concentration to 0.2M and adding 3 volumes of cold ethanol. The mixture was allowed to stand on ice (4° C.) for 10 minutes and the DNA precipitate was collected by centrifugation for 30 minutes at 10,000 ×g in a microfuge at 4° C. The DNA pellet was washed 2 times with 70% aqueous cold ethanol. The washed pellet was vacuum dried and dissolved in 10 μl water to which 2 μl of 10 ×ligation buffer, 2 μl of 1 mg/ml BSA, 6 μl of water and 1 unit $T_4$ DNA ligase were added. The mixture was incubated overnight at 4° C. and a 10 μl aliquot was used to transform *E. coli* DG75' (Maniatis, et al.) to obtain pHSA113ΔCla, which represents the deletion of HIS4 and 3' AOX1, along with small stretches of pBR322 sequences used to link these sequences. The deletion of the HIS4, 3' AOX1 and pBR322 sequences removes one of two Csp45I sites present in the pHSA113 vector. The remaining Csp45I site is in the AOXI 5' regulatory region (promoter).

B. Creation of pXHSA113ΔCla

Digest 5 μg of pHSA113ΔCla for 1 hour at 37° C. with 10 units of BstEII in 100 μl of REact 2 buffer. The digestion mixture was extracted with phenol and precipitated as detailed in step A. The DNA precipitate was dissolved in 100 μl of Csp45I buffer and digested at 37° C. for 2 hours in the presence of 10 units of Csp45I. The digested DNA was then phenol extracted and precipitated as described in step A. The DNA precipitate was dissolved in 20 μl of water and 10 μl aliquots were loaded on 2 neighboring wells of a 0.9% agarose gel. Following electrophoresis, the gel portion corresponding to one of the lanes was stained and this was used to locate the position of the Csp45I-BstEII fragment of pHSA113ΔCla in the unstained lane. The gel portion containing the larger Csp45I-BstEII fragment of pHSA113ΔCla was excised from the gel. The gel portion containing the larger Csp45I-BstEII fragment was electroeluted into 500 μl of 5 mM EDTA, pH 8.0. The DNA solution was phenol extracted as detailed in step A and the DNA precipitate was dissolved in 100 μl water. The larger Csp45I-BstEII fragment was then ligated with the BstEII-Csp45I oligonucleotide linker described below. An aliquot (10 μl) of the Csp45I-BstEII fragments was ligated overnight at 4° C. with 20 ng of annealed linker oligonucleotides 5'-CGAAACG ATG AAG TGG (SEQ ID NO:13) (nucleic acid) and SEQ ID NO: 14 (its corresponding amino acid sequence starting from the ATG start codon and 5'-GTTACCCACTTCATCGTTT (SEQ ID NO:15) in 20 μl ligase buffer containing 100 μg/ml BSA and 1 unit of $T_4$ DNA ligase. The ligation mixture was used to transform *E. coli* DG75' to obtain pXHSA113ΔCla. The pXHSA113ΔCla vector by virtue of the linker described above has an exact linkage between the 3' end of the native AOX1 5' regulatory region (promoter) and the HSA ATG start codon with no extraneous DNA sequences.

C. Creation of pHSA313

1 μg of pXHSA113ΔCla was digested for 4 hours at 37° C. with ClaI in 100 μl of REact 1 buffer. Following digestion the reaction mixture was adjusted to alkaline phosphatase buffer conditions and treated with 10 units of calf intestinal alkaline phosphatase in a 200 μl reaction volume for 30 minutes at 37° C. Phosphatase treatment was terminated by phenol extraction and the DNA was precipitated and dissolved in water at a concentration of approximately 10 ng/μl as described in step A and stored at −20° C.

1 μg of pAO807N (FIG. 8, construction of which is described in European Patent Application 0 344 459) was digested for 4 hours at 37° C. with PstI in 100 μl of REact 2 buffer. The digested DNA was adjusted to alkaline phosphatase buffer conditions and treated with 10 units of calf intestinal alkaline phosphatase in a 200 μl reaction volume for 15 minutes at 55° C. At the end of 15 minutes another 10 units of phosphatase was added and incubated for 15 minutes. Phosphatase treatment was terminated by phenol extraction and the DNA was precipitated as described in step A. DNA was digested for 4 hours at 37° C. with 5 units of ClaI in 100 μl REact 1 buffer containing 100 μg/ml BSA, followed by phenol extraction and precipitation of DNA as outlined in step A. The DNA precipitate was dissolved in water at a concentration of approximately 20 ng/μl. This ClaI fragment contains the HIS4 gene and 3' AOX1 second insertable sequence.

Approximately 100 ng (10 μl) of ClaI cleaved-phosphatased pXHSA113ΔCla was mixed with approximately 80 ng of PstI digested-phosphatased and ClaI-cleaved pAO807N (4' μl), 4 μl of 5×ligase buffer, 2 μl of 1 mg/ml BSA and ligated overnight at 4° C. using 1 unit of $T_4$ DNA ligase. The ligation mixture was used to transform *E. coli* DG75' to obtain pHSA313. The pHSA313 plasmid from this ligation contains the complete pXHSA113ΔCla sequence linked to the HIS4 gene and the AOXI 3' second insertable sequence derived from pAO807N. The relative orientation of the components of the pHSA313 plasmid is the same as that shown in FIG. 7 for plasmid pHSA113.

Example VII

Construction of 5' & 3' exact HSA expression plasmid pHSA413

The pHSA413 vector was constructed to provide a vector with an exact linkage between the 3' and of the AOX1 5' regulatory region and the start codon of the HSA structural gene as well as an exact linkage between the 5' end of the AOX1 3' termination sequence and the 3' end of the HSA structural gene.

A. Creation of pXXHSA113ΔCla

1 μg of pXHSA113ΔCla was digested for 4 hours at 37° C. with 10 units of EcoRI in 100 μl REact 3 buffer. The digestion mixture was phenol extracted and DNA precipitated as detailed in Example VI. DNA precipitate was dissolved in 20 μl water and digested for 1 hour at 37° C. with 20 units of Bsu36I in 100 μl of Bsu36I buffer. The digestion mixture was phenol extracted, DNA precipitated and dissolved in 100 μl of water as detailed in Example VI. Approximately 100 ng of EcoRI and Bsu36I-cleaved DNA was mixed with 10 ng of annealed oligonucleotides 5'-TTAGGCTTATAAG (SEQ ID NO:16) and 5'-AATTCTTATAAGCC (SEQ ID NO:17) and ligated overnight at 4° C. in 20 μl of $T_4$ DNA ligase buffer containing 100 μg/ml BSA and 10 units of $T_4$ DNA ligase. The ligation mixture was used to transform *E. coli* to obtain pXXHSA113ΔCla. In this plasmid the sequence between Bsu36I and EcoRI (SEQ ID NO:18) present in pXHSA113ΔCla shown below:

Bsu36I
5'CCTTAGGCTTATAACATCTCTACATTTAAAAGCATCTCAGCCTACCATGAGAATAAGAGAAAGAAAATGAAGATCA
AAAGCTTATTCATCTGTGTTTTCTTTTTCGTTGGTGTAAAGCCAACACCCTGTCTAAAAAACATAAATTTCTTTAATC
ATTTGCCTCTTTTTCTCTGTGCTTCAATTAATAAAAAATGGAAAGAATCTAAAAAAAAAAAAAAAAAAAGGAATTC

EcoRI is replaced by 5'CC TTA GGC TTA TAA GAATTC (SEQ ID NO:19)

Bsu36I      EcoRI

B. Creation of pHSA413

1 µg of pXXHSA113ΔCla was digested for 4 hours at 37° C. with ClaI in 100 µl of REact 1 buffer. Following digestion the reaction mixture was adjusted to alkaline phosphatase buffer conditions and treated with 10 units of calf intestinal alkaline phosphatase in 200 µl reaction volume for 30 minutes at 37° C. Phosphatase treatment was terminated by phenol extraction and the DNA was precipitated and dissolved in water at a concentration of approximately 10 ng/µl as described in step A and stored at −20° C.

Approximately 100 ng (10 µl) of ClaI cleaved-phosphatased pXXHSA113ΔCla was mixed with approximately 80 ng (4 µl) of PstI digested phosphatased and ClaI-cleaved pAO807N (see paragraph 2 in step 3 of Example VI), 4 µl of 5× ligase buffer, 2 µl of 1 mg/ml BSA and ligated overnight at 4° C. using 1 unit of $T_4$ DNA ligase. The ligation mixture was used to transform E. coli DG75' to obtain pHSA413. The pHSA413 plasmid from this ligation contains the complete pXXHSA113ΔCla sequence linked to the HIS4 gene and the AOX1 3' second insertable sequence derived from pAO807N. The relative orientation of the components of the pHSA413 plasmid is the same as that shown in FIG. 7 for plasmid pHSA113.

Example VIII

Transformation of Pichia pastoris with pHSA313 and pHSA413

A. Vector preparation

About 10 µg each of pHSA313, pHSA413, and pAO807N (negative control) were digested for 12 hours at 37° C. in 200 µl of HS buffer with 50 units of NotI. The digested DNA samples were phenol extracted, precipitated as described in Example VI, dissolved in 20 µl of CaS, and were then used for transformation of Pichia pastoris GS115. About 10 µg each of pHSA313, pHSA413, and pAO807N were also digested with 20 units of SstI for 12 hours at 37° C. in 200 µl of REact 2 buffer containing 100 µg/ml of BSA. The digested DNA samples were extracted with phenol, precipitated as described in Example VI and dissolved in 20 µl of CaS.

B. Cell Growth

Pichia pastoris GS115 (NRRL Y-15851) was inoculated into about 10 ml of YPD medium and shake cultured at 30° C. for 12–20 hours. 100 ml of YPD medium was inoculated with a seed culture to give an $OD_{600}$ of about 0.001. The medium was cultured in a shake flask at 30° C. for about 12–20 hours. The culture was harvested when the $OD_{600}$ was about 0.2–0.3 by centrifugation at 1555 g for 5 minutes using a Sorvall RB5C.

C. Preparation of Spheroplasts

The cells were washed in 10 ml of sterile water, and then centrifuged at 1500 g for 5 minutes. (Centrifugation is performed after each cell wash at 1500 g for 5 minutes using a Sorvall RT6000B unless otherwise indicated.) The cells were washed once in 10 ml of freshly prepared SED, once in 10 ml of sterile 1M sorbitol, and finally resuspended in 10 ml of SCE buffer. 7.5 µl of 3 mg/ml Zymolyase (100,000 units/g, obtained from Miles Laboratories) was added to the cell suspension. The cells were incubated at 30° C. for about 10 minutes. (A reduction of 60% in $OD_{600}$ in 5% SDS can be utilized as a correct time marker.) The spheroplasts were washed in 10 ml of sterile 1M sorbitol by centrifugation at 700 g for 5–10 minutes. 10 ml of sterile CaS was used as a final cell wash, and the cells were centrifuged again at 700 g for 5–10 minutes and then resuspended in 0.6 ml of CaS.

D. Transformation

Pichia pastoris GS115 cells were transformed with 10 µg of linearized DNA (see step A) using the spheroplast transformation technique of Sreekrishna et al., Gene 59, 115–125 (1987). DNA samples were added (up to 20 µl volume) to 12×75 mm sterile polypropylene tubes. (DNA should be in a suitable buffer such as TE buffer or CaS.) 100 µl of spheroplasts were added to each DNA sample and incubated at room temperature for about 20 minutes. 1 ml of PEG solution was added to each sample and incubated at room temperature for about 15 minutes and centrifuged at 700 g for 5–10 minutes. SOS (150 µl) was added to the pellet and incubated for 30 minutes at room temperature. Finally 850 µl of 1M sorbitol was added.

E. Regeneration of Spheroplasts

A bottom agarose layer of 20 ml of regeneration agar SDR was poured per plate at least 30 minutes before transformation samples were ready. In addition, 8 ml aliquots of regeneration agar were distributed to 15 ml conical bottom Corning tubes in a 45° C. water bath during the period that transformation samples were in SOS. Aliquots of 50 or 250 µl of the transformed sample was added to the 8 ml aliquots of molten regeneration agar held at 45° C. and poured onto plates containing the solid 20 ml bottom agar layer. The plates were incubated at 30° C. for 3–5 days.

F. Selection of Transformants

Transformants were selected for by culturing on SDR, a media lacking histidine. The colonies which grew in the absence of histidine were also screened for "methanol-slow" phenotype, indicating displacement of the AOX1 structural gene by the NotI DNA fragment) in the case of transformants obtained using NotI linearized vectors. Several transformed GS115 cells showing "methanol-normal" (those obtained with SstI linearized DNA) and methanol-slow were then cultured and assayed for the production of HSA.

Example IX

Methanol induced secretion of HSA in GS115/pHSA313, and GS115/pHSA413 Integrative Transformants Pichia pastoris GS115 strains transformed with pHSA313 and pHSA413 were analysed for HSA secretion in shake tube cultures. Both methanol-slow and methanol-normal strains were used. In each case 36 independent clones were studied. Transformants obtained with pAO807N served as negative controls. A protocol was developed to ensure efficient secretion and stable accumulation of HSA in the culture medium.

Cells were grown to saturation in 10 ml BMGR or BMGY, and were placed in 50 ml tubes (2–3 days). The cells would be in the range of 10–20 $A_{600}$ units. The cells were harvested, the supernatant liquid was discarded, and then the pellet was resuspended in 2 ml of BMMR or BMMY. The tube was covered with a sterile gauze (cheese cloth) instead of a cap. The tube(s) were then returned to a 30° C. shaker. At the end of 2–3 days, the cells were pelleted, and the supernatant assayed for product. The pellets could be resuspended with fresh medium and returned to the shaker for renewed secretion. With Pichia-HSA strains, 10 μl of media supernatant was sufficient for analysis by SDS-PAGE followed by Coomassie staining. Under these conditions a single band of 67 kD corresponding to HSA was observed. There was no significant difference between the expression levels of GS115/pHSA313 vs GS115/pHSA413 transformants, suggesting that deleting the 3' untranslated sequences from the HSA gene present in pHSA313 did not significantly affect expression levels. No significant difference in the HSA expression level was observed between methanol-slow vs methanol-normal transformants, in shake flask cultures. This suggests that disruption of AOX1 was not essential for efficient HSA expression. As expected, HSA was absent in both the culture medium and the cell extract of GS115/pAO807N transformants (negative control).

Example X

Batch-Fed Fermentation of Mut⁻ *Pichia pastoris* for Production of HSA

*Pichia pastoris* GS115:pHSA 413-6 was inoculated into a 20 liter Biolafitte fermentor with an 8.5 l working volume. The inoculum was prepared in the following manner: a culture was grown on a YM plate and then transferred to 100 ml YM broth in a shake flask and grown for about 24 hours. 50 mls of this culture was transferred to 1 liter of YM broth in a shake flask and also grown for about 24 hours. 1 liter of this was then transferred to 8.5 liters of fermentor medium in the Biolafitte fermentor. Fermentor medium consisted of Minimal salts+biotin+5 percent glycerol. Batch growth conditions included the following: pH=5.8 (controlled with $NH_3$), temperature=30° C., and percent dissolved oxygen greater than 20 percent air saturation.

Glycerol exhaustion was complete after about 24 hours, at which time a slow methanol feed was begun at a rate of 10–15 ml/hr. The methanol concentration was monitored in the fermentor and the feed rate was adjusted to maintain a concentration of 0.5–0.9 percent of methanol in the broth.

Secreted HSA in the media was measured quantitatively by desitometry of Coomassie blue stained polyacrylamide gels containing SDS (SDS-PAGE). Areas were referenced to a series of known weights of authentic HSA run on the same SDS-PAGE gels. The data from these gels is included in Table III.

TABLE III

Production of HSA by Batch-Fed Fermentation

| Run | Strain | Run pH | Hrs. MeOH | Dry Cell Wt. | HSA in Broth g/l |
|---|---|---|---|---|---|
| 1 | GS115:pHSA 413-6 | 5.79 | 101 | ND | 2.13 |
| 2 | GS115:pHSA 413-6 | 5.85 | 237 | 101 | 3.39 |
| 3 | G5115:pHSA 413-6 | 5.85 | 265 | 98.12 | 2.70 |
| 4 | GS115:pHSA 413-6 | 5.97 | 258 | 117 | 2.90 |

---

That which is claimed is:

1. An expression cassette for the Human Serum Albumin (HSA) in *Pichia pastoris* comprising:
   (a) the *Pichia pastoris* AOX1 5' regulatory region wherein said regulatory region is operably linked to
   (b) a HSA structural gene encoding a HSA signal sequence and a mature HSA protein, wherein the HSA structural gene has an ATG start codon within no more than 11 intervening deoxyribonucleotides at the 5' end of said HSA structural gene and wherein the adenine and thymine content of the intervening deoxyribonucleotides is in the range of from about 55 to about 64 percent and wherein said HSA structural gene is operably linked to
   (c) a functional 3' termination sequence.

2. The expression cassette of claim 1 wherein the expression cassette is incorporated into a vector selected from the group consisting of circular plasmids and linear plasmids.

3. The expression cassette of claim 2 wherein the vector is a integrative site-specific vector.

4. The expression cassette of claim 1 wherein the expression cassette is incorporated into a vector comprising the following serial arrangement:
   (a) a first insertable DNA fragment;
   (b) at least one marker gene; and
   (c) a second insertable DNA fragment;
   wherein at least one expression cassette is incorporated either before or after the marker gene of component (b), and the first and second insertable DNA fragments employed are homologous with separate portions of the *Pichia pastoris* genome and the insertable fragments are in the same relative orientation as exist in the *Pichia pastoris* genome.

5. The expression cassette of claim 4 wherein the first insertable DNA fragment and the second insertable DNA fragment are obtained from the DNA sequences of a gene isolated from *Pichia pastoris* selected form the group consisting of an AOX1 gene, a p40 gene, a DAS1 gene and an HIS4 gene.

6. The expression cassette of claim 4 wherein the marker gene is selected from the group consisting of a *Pichia pastoris* HIS4 gene, a *Pichia pastoris* ARG4 gene, a *Saccharomyces cerevisiae* SUC2 gene, a G418$^R$ gene of bacterial transposon Tn601 and a G418$^R$ gene of bacterial transposon Tn903.

7. The expression cassette of claim 4 wherein said vector comprises:
   (a) a first insertable DNA fragment which is the *Pichia pastoris* AOX1 5' regulatory region operably linked to
   (b) an HSA structural gene having an ATG start codon within no more than 8 deoxyribonucleotides of the end of the AOX1 regulatory region, operably linked to
   (c) the 3' termination sequence of the *Pichia pastoris* AOX1 gene; operably linked to
   (d) the *Pichia pastoris* HIS4 gene as a marker gene and operably linked to
   (e) a second insertable DNA fragment which is about 0.65 kilobases of the AOX1 termination sequence.

8. The expression cassette of claim 7 wherein the HSA structural gene has an ATG start codon with the deoxyribonucleotides AGGAATTC 5' of said ATG start codon.

9. The expression cassette of claim 7 wherein the HSA structural gene has no deoxynucleotides 5' of the ATG start codon.

10. A *Pichia pastoris* cell transformed with an expression cassette of claim 1.

11. The *Pichia pastoris* cell of claim 10 wherein the *Pichia pastoris* cell which is to be transformed is selected from the group consisting of *Pichia pastoris* GS115 (NRRL Y-15851), *Pichia pastoris* GS190 (NRRL Y-18014), *Pichia pastoris* PPF1 (NRRL Y-18017), *Pichia pastoris* (NRRL Y-11430) and *Pichia pastoris* (NRRL Y-14431).

12. The *Pichia pastoris* cell of claim 10 wherein the *Pichia pastoris* cell which is to be transformed is *Pichia pastoris* GS115 (NRRL Y-15851).

13. The *Pichia pastoris* cell of claim 10 wherein the expression cassette used for transformation utilizes the 3' termination sequence isolated from a *Pichia pastoris* gene selected from the group consisting of an AOX1 gene, a DAS1 gene, a p40 gene and a HIS4 gene.

14. The *Pichia pastoris* cell of claim 10 wherein the expression cassette is incorporated into a vector selected from the group consisting of circular plasmids and linear plasmids.

15. The *Pichia pastoris* cell of claim 14 wherein the vector utilized for transformation is an integrative site-specific vector.

16. The *Pichia pastoris* cell of claim 10 wherein the *Pichia pastoris* cell is transformed with an expression cassette which is incorporated into a vector comprising the following serial arrangement:
   (a) a first insertable DNA fragment;
   (b) at least one marker gene; and
   (c) a second insertable DNA fragment;
   wherein at least one expression cassette is incorporated either before or after the marker gene of component (b), and the first and second insertable DNA fragments employed are homologous with separate portions of the *Pichia pastoris* genome wherein the insertable fragments are in the same relative orientation as exist in the *Pichia pastoris* genome.

17. The *Pichia pastoris* cell of claim 16 wherein the *Pichia pastoris* cell is transformed with a vector having the first insertable DNA fragment and the second insertable DNA fragment obtained from the DNA sequences of a gene isolated from *Pichia pastoris* selected from the group consisting of an AOX1 gene, a p40 gene, a DAS1 gene and a HIS4 gene.

18. The *Pichia pastoris* cell of claim 16 wherein the *Pichia pastoris* cell is transformed with the vector which has a marker gene selected from the group consisting of a *Pichia pastoris* HIS4 gene, a *Pichia pastoris* ARG4 gene, a *Saccharomyces cerevisiae* SUC2 gene, a G418$^R$ gene of bacterial transposon Tn601 and a G418$^R$ gene of bacterial transposon Tn903.

19. A *Pichia pastoris* cell transformed with the vector of claim 7.

20. The expression cassette of claim 19 wherein the HSA structural gene has an ATG start codon with the deoxyribonucleotides AGGAATTC 5' of said start codon.

21. The expression cassette of claim 19 wherein the HSA structural gene has no deoxynucleotides 5' of the ATG start codon.

22. A process for the secretion of Human Serum Albumin (HSA) comprising: transforming a *Pichia pastoris* cell with at least one vector having at least one expression cassette comprising:
   (a) the *Pichia pastoris* AOX1 5' regulatory region wherein said regulatory region is operably linked to
   (b) an HSA structural gene encoding a HSA signal and a mature HSA protein, wherein the HSA structural gene has an ATG start codon within no more than 11 intervening deoxyribonucleotides at the 5' end of said HSA structural gene and wherein the adenine and thymine content of the intervening deoxyribonucleotides is the range of from about 55 to about 64 percent and wherein said HSA structural gene is operably linked to
   (c) a functional 3' termination sequence and thereafter culturing the resulting transformed *Pichia pastoris* cell under suitable conditions to obtain the production of HSA.

23. The process of claim 22 wherein the *Pichia pastoris* cell utilized to produce HSA is transformed with said at least one expression cassette which utilizes the AOX1 5' regulatory region from *Pichia pastoris*.

24. The process of claim 22 wherein the *Pichia pastoris* cell utilized to produce HSA is transformed with an expression cassette containing a 3' termination sequence isolated from a *Pichia pastoris* gene selected from the group consisting of an AOX1 gene, a DAS1 gene, a p40 gene and a HIS4 gene.

25. The process of claim 22 wherein the *Pichia pastoris* cell which is to be transformed is selected from the group consisting of *Pichia pastoris* GS115 (NRRL Y-15851), *Pichia pastoris* GS190 (NRRL Y-18014), *Pichia pastoris* PPF1(NRRL Y-18017), *Pichia pastoris* (NRRL Y-11430) and (NRRL Y-11431).

26. The process of claim 25 wherein *Pichia pastoris* cell which is to be transformed is *Pichia pastoris* GS115 (NRRL Y-15851).

27. The process of claim 22 wherein the vector utilized to transform said *Pichia pastoris* cell is selected from the group consisting of circular plasmids and linear plasmids.

28. The process of claim 27 wherein the vector utilized to transform said *Pichia pastoris* cell is an integrative site-specific vector.

29. The process of claim 27 wherein the integrative site-specific vector utilized to transform said *Pichia pastoris* cell contains the following serial arrangement:

a) a first insertable DNA fragment;

b) at least one marker gene; and c) a second insertable DNA fragment;

wherein at least one expression cassette is incorporated either before or after the marker gene of component (b), and the first and second insertable DNA fragments employed are homologous with separate portions of the *Pichia pastoris* genome and the insertable fragments are in the same relative orientation as exist in the *Pichia pastoris* genome.

30. The process of claim 29 wherein the first insertable DNA fragment and the second insertable DNA fragment are obtained from the DNA sequence of a gene isolated from *Pichia pastoris* and selected from the group consisting of an AOX1 gene, a p40 gene, a DAS1 gene and a HIS4 gene.

31. The process of claim 29 wherein the marker gene is selected from the group consisting of a *Pichia pastoris* HIS4 gene, a *Pichia pastoris* ARG4 gene, a *Saccharomyces cerevisiae* SUC2 gene, a G418$^R$ gene of bacterial transposon Tn601 and a G418$^R$ gene of bacterial transposon Tn903.

32. The process of claim 29 wherein said vector comprises:

a) a first insertable DNA fragment which is about one kilobase of the AOX1 5' regulatory region isolated from *Pichia pastoris* operably linked to b) an HSA structural gene encoding an HSA signal sequence and a mature HSA protein having a 5' end and a 3' end wherein the HSA structural gene has an ATG start codon within no more than 8 deoxyribonucleotides of the 5' end of said HSA structural gene; operably linked to c) the 3' termination sequence of the AOX1 gene isolated from *Pichia pastoris*; operably linked to d) a marker gene which is the HIS4 gene isolated from *Pichia pastoris*; operably linked to e) a second insertable DNA fragment which is about 0.65 kilobases for the AOX1 3' termination sequence.

33. The expression cassette of claim 32 wherein the HSA structural gene has an ATG start codon with the deoxyribonucleotides AGGAATTC 5' of said ATG start codon.

34. The expression cassette of claim 32 wherein the HSA structural has no deoxynucleotides 5' of the ATG start codon.

* * * * *

UNITED STATES PATENT AND TRADEMARK OFFICE
CERTIFICATE OF CORRECTION

PATENT NO.     : 5,707,828
DATED          : January 13, 1998
INVENTOR(S)    : K. Sreekrishna, et al.

Page 1 of 1

It is certified that error appears in the above-identified patent and that said Letters Patent is hereby corrected as shown below:

Title page, item [56] References Cited,
OTHER PUBLICATIONS, line 13, after -- 1121 --, insert -- (May 1985) --
OTHER PUBLICATIONS, after "E. coli, "Nuc. Acid Res.", insert -- Bio/Technology, 6: 1309-1314 (December 1987). R. Lawn, "The Sequence of Human Serum Albumin cDNA and it's Expression in E. coli," --

Column 14,
Line 37, "CaC12" should read -- $CaCl_2$ --

Column 18,
Line 25, "G + H5A14053" should read -- G + HSA140S3 --

Column 19,
Line 55, "codon" should read -- codon) --

Column 22,
Line 60, "Pichla" should read -- Pichia --

Column 39, Claim 1,
Line 49, "the Human Serum" should read -- the production of Human Serum --

Signed and Sealed this

Eleventh Day of September, 2001

Attest:

NICHOLAS P. GODICI
*Attesting Officer*     *Acting Director of the United States Patent and Trademark Office*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 940 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGATCTAACA  TCCAAAGACG  AAAGGTTGAA  TGAAACCTTT  TTGCCATCCG  ACATCCACAG      60

GTCCATTCTC  ACACATAAGT  GCCAAACGCA  ACAGGAGGGG  ATACACTAGC  AGCAGACCGT     120

TGCAAACGCA  GGACCTCCAC  TCCTCTTCTC  CTCAACACCC  ACTTTTGCCA  TCGAAAAACC     180

AGCCCAGTTA  TTGGGCTTGA  TTGGAGCTCG  CTCATTCCAA  TTCCTTCTAT  TAGGCTACTA     240

ACACCATGAC  TTTATTAGCC  TGTCTATCCT  GGCCCCCCTG  GCGAGGTTCA  TGTTTGTTTA     300

TTTCCGAATG  CAACAAGCTC  CGCATTACAC  CCGAACATCA  CTCCAGATGA  GGGCTTTCTG     360
```

-continued

```
AGTGTGGGGT CAAATAGTTT CATGTTCCCC AAATGGCCCA AAACTGACAG TTTAAACGCT     420

GTCTTGGAAC CTAATATGAC AAAAGCGTGA TCTCATCCAA GATGAACTAA GTTTGGTTCG     480

TTGAAATGCT AACGGCCAGT TGGTCAAAAA GAAACTTCCA AAAGTCGGCA TACCGTTTGT     540

CTTGTTTGGT ATTGATTGAC GAATGCTCAA AAATAATCTC ATTAATGCTT AGCGCAGTCT     600

CTCTATCGCT TCTGAACCCC GGTGCACCTG TGCCGAAACG CAAATGGGGA ACACCCGCT     660

TTTTGGATGA TTATGCATTG TCTCCACATT GTATGCTTCC AAGATTCTGG TGGGAATACT     720

GCTGATAGCC TAACGTTCAT GATCAAAATT TAACTGTTCT AACCCCTACT TGACAGCAAT     780

ATATAAACAG AAGGAAGCTG CCCTGTCTTA AACCTTTTTT TTTATCATCA TTATTAGCTT     840

ACTTTCATAA TTGCGACTGG TTCCAATTGA CAAGCTTTTG ATTTAACGA CTTTTAACGA     900

CAACTTGAGA AGATCAAAAA ACAACTAATT ATTCGAAACG                          940
```

(2) INFORMATION FOR SEQ ID NO:2:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
AAAGTAAACC CCATTCAATG TTCCGAGATT TAGTATACTT GCCCTATAA GAAACGAAGG      60

ATTTCAGCTT CCTTACCCCA TGAACAGAAA TCTTCCATTT ACCCCCCACT GGAGAGATCC    120

GCCCAAACGA ACAGATAATA GAAAAAGAA ATTCGGACAA ATAGAACACT TTCTCAGCCA     180

ATTAAAGTCA TTCCATGCAC TCCCTTTAGC TGCCGTTCCA TCCCTTTGTT GAGCAACACC    240

ATCGTTAGCC AGTACGAAAG AGGAAACTTA ACCGATACCT GGAGAAATC TAAGGCGCGA     300

ATGAGTTTAG CCTAGATATC CTTAGTGAAG GGTGTTCCGA TACCTTCTCC ACATTCAGTC    360

ATAGATGGGC AGCTTTGTTA TCATGAAGAG ACGGAAACGG GCATTAAGGG TTAACCGCCA    420

AATTATATAA AAGACAACAT GTCCCAGTT TAAAGTTTTT CTTTCCTATT CTTGTATCCT     480

GAGTGACCGT TGTGTTTAAT ATAACAAGTT CGTTTAACT TAAGACCAAA ACCAGTTACA     540

ACAAATTATA ACCCTCTAA ACACTAAAGT TCACTCTTAT CAAACTATCA AACATCAAAA     600
```

(2) INFORMATION FOR SEQ ID NO:3:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1827

(xi) SEQUENCE DESCRIPTION: SEQ ID NO:3:

```
ATG  AAG  TGG  GTA  ACC  TTT  ATT  TCC  CTT  CTT  TTT  CTC  TTT  AGC  TCG  GCT     48
Met  Lys  Trp  Val  Thr  Phe  Ile  Ser  Leu  Leu  Phe  Leu  Phe  Ser  Ser  Ala
 1                   5                        10                      15

TAT  TCC  AGG  GGT  GTG  TTT  CGT  CGA  GAT  GCA  CAC  AAG  AGT  GAG  GTT  GCT     96
Tyr  Ser  Arg  Gly  Val  Phe  Arg  Arg  Asp  Ala  His  Lys  Ser  Glu  Val  Ala
                20                       25                      30

CAT  CGG  TTT  AAA  GAT  TTG  GGA  GAA  GAA  AAT  TTC  AAA  GCC  TTG  GTG  TTG    144
```

```
            His Arg Phe Lys Asp Leu Gly Glu Glu Asn Phe Lys Ala Leu Val Leu
                     35              40                  45

ATT GCC TTT GCT CAG TAT CTT CAG CAG TGT CCA TTT GAA GAT CAT GTA              192
Ile Ala Phe Ala Gln Tyr Leu Gln Gln Cys Pro Phe Glu Asp His Val
        50              55                  60

AAA TTA GTG AAT GAA GTA ACT GAA TTT GCA AAA ACA TGT GTT GCT GAT              240
Lys Leu Val Asn Glu Val Thr Glu Phe Ala Lys Thr Cys Val Ala Asp
 65              70                  75                      80

GAG TCA GCT GAA AAT TGT GAC AAA TCA CTT CAT ACC CTT TTT GGA GAC              288
Glu Ser Ala Glu Asn Cys Asp Lys Ser Leu His Thr Leu Phe Gly Asp
                     85                  90                  95

AAA TTA TGC ACA GTT GCA ACT CTT CGT GAA ACC TAT GGT GAA ATG GCT              336
Lys Leu Cys Thr Val Ala Thr Leu Arg Glu Thr Tyr Gly Glu Met Ala
            100                 105                 110

GAC TGC TGT GCA AAA CAA GAA CCT GAG AGA AAT GAA TGC TTC TTG CAA              384
Asp Cys Cys Ala Lys Gln Glu Pro Glu Arg Asn Glu Cys Phe Leu Gln
        115                 120                 125

CAC AAA GAT GAC AAC CCA AAC CTC CCC CGA TTG GTG AGA CCA GAG GTT              432
His Lys Asp Asp Asn Pro Asn Leu Pro Arg Leu Val Arg Pro Glu Val
    130                 135                 140

GAT GTG ATG TGC ACT GCT TTT CAT GAC AAT GAA GAG ACA TTT TTG AAA              480
Asp Val Met Cys Thr Ala Phe His Asp Asn Glu Glu Thr Phe Leu Lys
145                 150                 155                 160

AAA TAC TTA TAT GAA ATT GCC AGA AGA CAT CCT TAC TTT TAT GCC CCG              528
Lys Tyr Leu Tyr Glu Ile Ala Arg Arg His Pro Tyr Phe Tyr Ala Pro
                165                 170                 175

GAA CTC CTT TTC TTT GCT AAA AGG TAT AAA GCT GCT TTT ACA GAA TGT              576
Glu Leu Leu Phe Phe Ala Lys Arg Tyr Lys Ala Ala Phe Thr Glu Cys
            180                 185                 190

TGC CAA GCT GCT GAT AAA GCT GCC TGC CTG TTG CCA AAG CTC GAT GAA              624
Cys Gln Ala Ala Asp Lys Ala Ala Cys Leu Leu Pro Lys Leu Asp Glu
        195                 200                 205

CTT CGG GAT GAA GGG AAG GTT TCG TCT GCC AAA CAG AGA CTC AAG TGT              672
Leu Arg Asp Glu Gly Lys Val Ser Ser Ala Lys Gln Arg Leu Lys Cys
    210                 215                 220

GCC AGT CTC CAA AAA TTT GGA GAA AGA GCT TTC AAA GCA TGG GCA GTA              720
Ala Ser Leu Gln Lys Phe Gly Glu Arg Ala Phe Lys Ala Trp Ala Val
225                 230                 235                 240

GCT CGC CTG AGC CAG AGA TTT CCC AAA GCT GAG TTT GCA GAA GTT TCC              768
Ala Arg Leu Ser Gln Arg Phe Pro Lys Ala Glu Phe Ala Glu Val Ser
                245                 250                 255

AAG TTA GTG ACA GAT CTT ACC AAA GTC CAC ACG GAA TGC TGC CAT GGA              816
Lys Leu Val Thr Asp Leu Thr Lys Val His Thr Glu Cys Cys His Gly
            260                 265                 270

GAT CTG CTT GAA TGT GCT GAT GAC AGG GCG GAC CTT GCC AAG TAT ATC              864
Asp Leu Leu Glu Cys Ala Asp Asp Arg Ala Asp Leu Ala Lys Tyr Ile
        275                 280                 285

TGT GAA AAT CAA GAT TCG ATC TCC AGT AAA CTG AAG GAA TGC TGT GAA              912
Cys Glu Asn Gln Asp Ser Ile Ser Ser Lys Leu Lys Glu Cys Cys Glu
    290                 295                 300

AAA CCT CTG TTG GAA AAA TCC CAC TGC ATT GCC GAA GTG GAA AAT GAT              960
Lys Pro Leu Leu Glu Lys Ser His Cys Ile Ala Glu Val Glu Asn Asp
305                 310                 315                 320

GAG ATG CCT GCT GAC TTG CCT TCA TTA GCT GCT GAT TTT GTT GAA AGT             1008
Glu Met Pro Ala Asp Leu Pro Ser Leu Ala Ala Asp Phe Val Glu Ser
                325                 330                 335

AAG GAT GTT TGC AAA AAC TAT GCT GAG GCA AAG GAT GTC TTC TTG GGC             1056
Lys Asp Val Cys Lys Asn Tyr Ala Glu Ala Lys Asp Val Phe Leu Gly
            340                 345                 350

ATG TTT TTG TAT GAA TAT GCA AGA AGG CAT CCT GAT TAC TCT GTC GTG             1104
```

```
            Met Phe Leu Tyr Glu Tyr Ala Arg Arg His Pro Asp Tyr Ser Val Val
                    355             360             365

CTG CTG CTG AGA CTT GCC AAG ACA TAT GAA ACC ACT CTA GAG AAG TGC        1152
Leu Leu Leu Arg Leu Ala Lys Thr Tyr Glu Thr Thr Leu Glu Lys Cys
        370             375             380

TGT GCC GCT GCA GAT CCT CAT GAA TGC TAT GCC AAA GTG TTC GAT GAA        1200
Cys Ala Ala Ala Asp Pro His Glu Cys Tyr Ala Lys Val Phe Asp Glu
385             390             395             400

TTT AAA CCT CTT GTG GAA GAG CCT CAG AAT TTA ATC AAA CAA AAT TGT        1248
Phe Lys Pro Leu Val Glu Glu Pro Gln Asn Leu Ile Lys Gln Asn Cys
                405             410             415

GAG CTT TTT GAG CAG CTT GGA GAG TAC AAA TTC CAG AAT GCG CTA TTA        1296
Glu Leu Phe Glu Gln Leu Gly Glu Tyr Lys Phe Gln Asn Ala Leu Leu
            420             425             430

GTT CGT TAC ACC AAG AAA GTA CCC CAA GTG TCA ACT CCA ACT CTT GTA        1344
Val Arg Tyr Thr Lys Lys Val Pro Gln Val Ser Thr Pro Thr Leu Val
            435             440             445

GAG GTC TCA AGA AAC CTA GGA AAA GTG GGC AGC AAA TGT TGT AAA CAT        1392
Glu Val Ser Arg Asn Leu Gly Lys Val Gly Ser Lys Cys Cys Lys His
450             455             460

CCT GAA GCA AAA AGA ATG CCC TGT GCA GAA GAC TAT CTA TCC GTG GTC        1440
Pro Glu Ala Lys Arg Met Pro Cys Ala Glu Asp Tyr Leu Ser Val Val
465             470             475             480

CTG AAC CAG TTA TGT GTG TTG CAT GAG AAA ACG CCA GTA AGT GAC AGA        1488
Leu Asn Gln Leu Cys Val Leu His Glu Lys Thr Pro Val Ser Asp Arg
                485             490             495

GTC ACC AAA TGC TGC ACA GAA TCC TTG GTG AAC AGG CGA CCA TGC TTT        1536
Val Thr Lys Cys Cys Thr Glu Ser Leu Val Asn Arg Arg Pro Cys Phe
            500             505             510

TCA GCT CTG GAA GTC GAT GAA ACA TAC GTT CCC AAA GAG TTT AAT GCT        1584
Ser Ala Leu Glu Val Asp Glu Thr Tyr Val Pro Lys Glu Phe Asn Ala
            515             520             525

GAA ACA TTC ACC TTC CAT GCA GAT ATA TGC ACA CTT TCT GAG AAG GAG        1632
Glu Thr Phe Thr Phe His Ala Asp Ile Cys Thr Leu Ser Glu Lys Glu
        530             535             540

AGA CAA ATC AAG AAA CAA ACT GCA CTT GTT GAG CTT GTG AAA CAC AAG        1680
Arg Gln Ile Lys Lys Gln Thr Ala Leu Val Glu Leu Val Lys His Lys
545             550             555             560

CCC AAG GCA ACA AAA GAG CAA CTG AAA GCT GTT ATG GAT GAT TTC GCA        1728
Pro Lys Ala Thr Lys Glu Gln Leu Lys Ala Val Met Asp Asp Phe Ala
            565             570             575

GCT TTT GTA GAG AAG TGC TGC AAG GCT GAC GAT AAG GAG ACC TGC TTT        1776
Ala Phe Val Glu Lys Cys Cys Lys Ala Asp Asp Lys Glu Thr Cys Phe
            580             585             590

GCC GAG GAG GGT AAA AAA CTT GTT GCT GCA AGT CAA GCT GCC TTA GGC        1824
Ala Glu Glu Gly Lys Lys Leu Val Ala Ala Ser Gln Ala Ala Leu Gly
        595             600             605

TTA TAA                                                                 1830
Leu
```

( 2 ) INFORMATION FOR SEQ ID NO:4:

( i ) SEQUENCE CHARACTERISTICS:
        ( A ) LENGTH: 609 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Trp Val Thr Phe Ile Ser Leu Leu Phe Leu Phe Ser Ser Ala
 1               5                  10                  15
```

Tyr Ser Arg Gly Val Phe Arg Arg Asp Ala His Lys Ser Glu Val Ala
                20                25                30
His Arg Phe Lys Asp Leu Gly Glu Glu Asn Phe Lys Ala Leu Val Leu
            35                40                45
Ile Ala Phe Ala Gln Tyr Leu Gln Gln Cys Pro Phe Glu Asp His Val
        50                55                60
Lys Leu Val Asn Glu Val Thr Glu Phe Ala Lys Thr Cys Val Ala Asp
65                  70                75                    80
Glu Ser Ala Glu Asn Cys Asp Lys Ser Leu His Thr Leu Phe Gly Asp
                85                90                95
Lys Leu Cys Thr Val Ala Thr Leu Arg Glu Thr Tyr Gly Glu Met Ala
            100               105               110
Asp Cys Cys Ala Lys Gln Glu Pro Glu Arg Asn Glu Cys Phe Leu Gln
        115               120               125
His Lys Asp Asp Asn Pro Asn Leu Pro Arg Leu Val Arg Pro Glu Val
    130               135               140
Asp Val Met Cys Thr Ala Phe His Asp Asn Glu Glu Thr Phe Leu Lys
145               150               155               160
Lys Tyr Leu Tyr Glu Ile Ala Arg Arg His Pro Tyr Phe Tyr Ala Pro
                165               170               175
Glu Leu Leu Phe Phe Ala Lys Arg Tyr Lys Ala Ala Phe Thr Glu Cys
            180               185               190
Cys Gln Ala Ala Asp Lys Ala Ala Cys Leu Leu Pro Lys Leu Asp Glu
        195               200               205
Leu Arg Asp Glu Gly Lys Val Ser Ser Ala Lys Gln Arg Leu Lys Cys
    210               215               220
Ala Ser Leu Gln Lys Phe Gly Glu Arg Ala Phe Lys Ala Trp Ala Val
225               230               235               240
Ala Arg Leu Ser Gln Arg Phe Pro Lys Ala Glu Phe Ala Glu Val Ser
                245               250               255
Lys Leu Val Thr Asp Leu Thr Lys Val His Thr Glu Cys Cys His Gly
            260               265               270
Asp Leu Leu Glu Cys Ala Asp Asp Arg Ala Asp Leu Ala Lys Tyr Ile
        275               280               285
Cys Glu Asn Gln Asp Ser Ile Ser Ser Lys Leu Lys Glu Cys Cys Glu
    290               295               300
Lys Pro Leu Leu Glu Lys Ser His Cys Ile Ala Glu Val Glu Asn Asp
305               310               315               320
Glu Met Pro Ala Asp Leu Pro Ser Leu Ala Ala Asp Phe Val Glu Ser
                325               330               335
Lys Asp Val Cys Lys Asn Tyr Ala Glu Ala Lys Asp Val Phe Leu Gly
            340               345               350
Met Phe Leu Tyr Glu Tyr Ala Arg Arg His Pro Asp Tyr Ser Val Val
        355               360               365
Leu Leu Leu Arg Leu Ala Lys Thr Tyr Glu Thr Thr Leu Glu Lys Cys
    370               375               380
Cys Ala Ala Ala Asp Pro His Glu Cys Tyr Ala Lys Val Phe Asp Glu
385               390               395               400
Phe Lys Pro Leu Val Glu Glu Pro Gln Asn Leu Ile Lys Gln Asn Cys
                405               410               415
Glu Leu Phe Glu Gln Leu Gly Glu Tyr Lys Phe Gln Asn Ala Leu Leu
            420               425               430
Val Arg Tyr Thr Lys Lys Val Pro Gln Val Ser Thr Pro Thr Leu Val

-continued

| | | 435 | | | | 440 | | | | 445 | | | | |
|---|---|---|---|---|---|---|---|---|---|---|---|---|---|---|
| Glu | Val | Ser | Arg | Asn | Leu | Gly | Lys | Val | Gly | Ser | Lys | Cys | Cys | Lys | His |
| | 450 | | | | | 455 | | | | 460 | | | | |
| Pro | Glu | Ala | Lys | Arg | Met | Pro | Cys | Ala | Glu | Asp | Tyr | Leu | Ser | Val | Val |
| 465 | | | | | 470 | | | | 475 | | | | | 480 | |
| Leu | Asn | Gln | Leu | Cys | Val | Leu | His | Glu | Lys | Thr | Pro | Val | Ser | Asp | Arg |
| | | | | 485 | | | | | 490 | | | | | 495 | |
| Val | Thr | Lys | Cys | Cys | Thr | Glu | Ser | Leu | Val | Asn | Arg | Arg | Pro | Cys | Phe |
| | | | 500 | | | | | 505 | | | | | 510 | | |
| Ser | Ala | Leu | Glu | Val | Asp | Glu | Thr | Tyr | Val | Pro | Lys | Glu | Phe | Asn | Ala |
| | | | 515 | | | | | 520 | | | | | 525 | | |
| Glu | Thr | Phe | Thr | Phe | His | Ala | Asp | Ile | Cys | Thr | Leu | Ser | Glu | Lys | Glu |
| | 530 | | | | | 535 | | | | | 540 | | | | |
| Arg | Gln | Ile | Lys | Lys | Gln | Thr | Ala | Leu | Val | Glu | Leu | Val | Lys | His | Lys |
| 545 | | | | | 550 | | | | | 555 | | | | | 560 |
| Pro | Lys | Ala | Thr | Lys | Glu | Gln | Leu | Lys | Ala | Val | Met | Asp | Asp | Phe | Ala |
| | | | | 565 | | | | | 570 | | | | | 575 | |
| Ala | Phe | Val | Glu | Lys | Cys | Cys | Lys | Ala | Asp | Asp | Lys | Glu | Thr | Cys | Phe |
| | | | 580 | | | | | 585 | | | | | 590 | | |
| Ala | Glu | Glu | Gly | Lys | Lys | Leu | Val | Ala | Ala | Ser | Gln | Ala | Ala | Leu | Gly |
| | | 595 | | | | | 600 | | | | | 605 | | | |
| Leu | | | | | | | | | | | | | | | |

( 2 ) INFORMATION FOR SEQ ID NO:5:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 22..36

( x i ) SEQUENCE DESCRIPTION: SEQ ID NO:5:

```
CCCTCACACG CCTTTGAATT C ATG AAG TGG GTA ACC                      36
                        Met Lys Trp Val Thr
                         1           5
```

( 2 ) INFORMATION FOR SEQ ID NO:6:

( i ) SEQUENCE CHARACTERISTICS:
( A ) LENGTH: 5 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Lys Trp Val Thr
 1           5
```

( 2 ) INFORMATION FOR SEQ ID NO:7:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
             ( A ) NAME/KEY: CDS
             ( B ) LOCATION: 1..12

( x i ) SEQUENCE DESCRIPTION: SEQ ID NO:7:

GCC TTA GGC TTA TAAGAATTCA GTTTAAAAGC ATCTCAG       39
Ala Leu Gly Leu
 1

( 2 ) INFORMATION FOR SEQ ID NO:8:

( i ) SEQUENCE CHARACTERISTICS:
             ( A ) LENGTH: 4 amino acids
             ( B ) TYPE: amino acid
             ( D ) TOPOLOGY: linear ( i i ) MOLECULE TYPE: protein ( x i ) SEQUENCE DESCRIPTION: SEQ ID NO:8:

Ala Leu Gly Leu
 1

( 2 ) INFORMATION FOR SEQ ID NO:9:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( i i ) MOLECULE TYPE: DNA (genomic)

( i x ) FEATURE:
             ( A ) NAME/KEY: CDS
             ( B ) LOCATION: 13..18

( x i ) SEQUENCE DESCRIPTION: SEQ ID NO:9:

GCCTGGGAAT TC ATG AAG                               18
              Met Lys
               1

( 2 ) INFORMATION FOR SEQ ID NO:10:

( i ) SEQUENCE CHARACTERISTICS:
             ( A ) LENGTH: 2 amino acids
             ( B ) TYPE: amino acid
             ( D ) TOPOLOGY: linear ( i i ) MOLECULE TYPE: protein ( x i ) SEQUENCE DESCRIPTION: SEQ ID NO:10:

Met Lys
 1

( 2 ) INFORMATION FOR SEQ ID NO:11:

( i ) SEQUENCE CHARACTERISTICS:
             ( A ) LENGTH: 18 base pairs
             ( B ) TYPE: nucleic acid
             ( C ) STRANDEDNESS: single
             ( D ) TOPOLOGY: linear ( i i ) MOLECULE TYPE: DNA (genomic)

( i x ) FEATURE:
             ( A ) NAME/KEY: CDS
             ( B ) LOCATION: 1..3

( x i ) SEQUENCE DESCRIPTION: SEQ ID NO:11:

TTA TAAGAATTCA GTTTA                                18

Leu
1

( 2 ) INFORMATION FOR SEQ ID NO:12:

( i ) SEQUENCE CHARACTERISTICS:
      ( A ) LENGTH: 1 amino acids
      ( B ) TYPE: amino acid
      ( D ) TOPOLOGY: linear ( i i ) MOLECULE TYPE: protein ( x i ) SEQUENCE DESCRIPTION: SEQ ID NO:12:

Leu
1

( 2 ) INFORMATION FOR SEQ ID NO:13:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 8..16

( x i ) SEQUENCE DESCRIPTION: SEQ ID NO:13:

CGAAACG ATG AAG TGG                                                    16
        Met Lys Trp
         1

( 2 ) INFORMATION FOR SEQ ID NO:14:

( i ) SEQUENCE CHARACTERISTICS:
      ( A ) LENGTH: 3 amino acids
      ( B ) TYPE: amino acid
      ( D ) TOPOLOGY: linear ( i i ) MOLECULE TYPE: protein ( x i ) SEQUENCE DESCRIPTION: SEQ ID NO:14:

Met Lys Trp
 1

( 2 ) INFORMATION FOR SEQ ID NO:15:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

GTTACCCACT TCATCGTTT                                                   19

( 2 ) INFORMATION FOR SEQ ID NO:16:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:16:

TTAGGCTTAT AAG                                                                                      13

( 2 ) INFORMATION FOR SEQ ID NO:17:

( i ) SEQUENCE CHARACTERISTICS:
     ( A ) LENGTH: 14 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:17:

AATTCTTATA AGCC                                                                                     14

( 2 ) INFORMATION FOR SEQ ID NO:18:

( i ) SEQUENCE CHARACTERISTICS:
     ( A ) LENGTH: 231 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:18:

CCTTAGGCTT ATAACATCTC TACATTTAAA AGCATCTCAG CCTACCATGA GAATAAGAGA         60

AAGAAAATGA AGATCAAAAG CTTATTCATC TGTGTTTTCT TTTTCGTTGG TGTAAAGCCA        120

ACACCCTGTC TAAAAAACAT AAATTTCTTT AATCATTTTG CCTCTTTTTC TCTGTGCTTC        180

AATTAATAAA AAATGGAAAG AATCTAAAAA AAAAAAAAA AAAAGGAATT C                  231

( 2 ) INFORMATION FOR SEQ ID NO:19:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:19:

CCTTAGGCTT ATAAGAATTC                                                                                20